(12) United States Patent
Mani

(10) Patent No.: US 6,221,225 B1
(45) Date of Patent: *Apr. 24, 2001

(54) APPARATUS AND PROCESS FOR ELECTRODIALYSIS OF SALTS

(75) Inventor: K. N. Mani, Basking Ridge, NJ (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/922,587

(22) Filed: Sep. 3, 1997

Related U.S. Application Data

(63) Continuation-in-part of application No. 08/787,899, filed on Jan. 23, 1997.
(51) Int. Cl.[7] ................................................. B01D 61/44
(52) U.S. Cl. .......................... 204/523; 204/525; 204/529; 204/530; 204/531
(58) Field of Search ..................................... 204/633, 634, 204/631, 647, 523, 525, 529, 530, 531, 534, 537, 538

(56) References Cited

U.S. PATENT DOCUMENTS 5,746,920 * 5/1998 Boergardts et al. .................. 204/537
5,814,498 * 9/1998 Mani et al. ........................... 204/527

* cited by examiner

*Primary Examiner*—Arun S. Phasge
(74) *Attorney, Agent, or Firm*—Laff, Whitesel & Saret, Ltd.; J. Warren Whitesel

(57) ABSTRACT

An apparatus and process produces salts by an electrodialysis operation. The basic electrodialysis apparatus is a cell having a number of compartments separated by ion exchange membranes. A DC source is connected to drive a current through a feed stream passing through the cell which splits the salt stream into an acid and a base. The incoming feed may be nanofiltered to remove divalent metal. The base loop may be in communication with an ion exchange column packed with a material that removes multivalent cations. Monovalent selctive cation membranes may be used to effect preferential treatment of the monovalent cations to the base loop. Depending upon the material being processed and the desired end result either or both the nanofiltration and the ion exchanged column may be used in the apparatus.

21 Claims, 15 Drawing Sheets

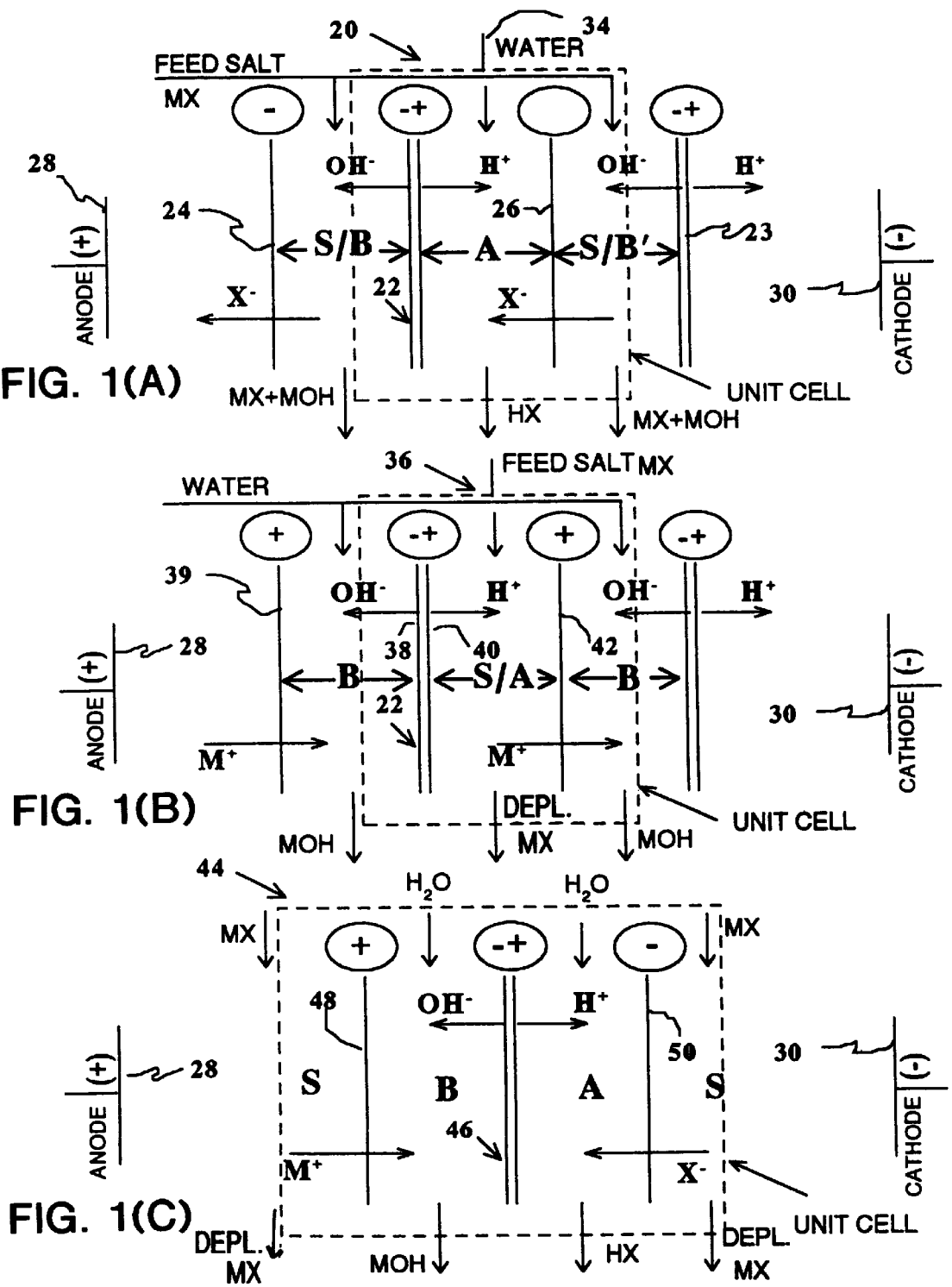

APPARATUS AND PROCESS FOR ELECTRODIALYSIS OF SALTS

This application is a Continuation-in-part of Ser. No. 08/787,899, Filed Jan. 23, 1997.

FIELD OF THE INVENTION

This invention relates to apparatus and processes for electrodialysis of salts and more particularly to apparatus and processes that incorporate at least one of three distinct features: a nanofiltration unit combined with an electrodialysis unit, ion exchange column connected to and in communication with the base loop of an electrodialysis cell, and the use of certain types of cation membranes in said electrodialysis cells.

This electrodialysis apparatus can be used in a number of large scale process applications. Specifically, it may be used for the recovery of lactic acid from fermentation derived ammonium lactate in a two compartment cation cell. There may be either a nanofilter or an ion exchange column (or both) in communication with the base loop of the electrodialysis cell. The column contains a weak acid cation exchange resin.

For more information on the background of the inventive structure, reference may be made to my co-pending applications having the following identifications: Process for the Recovery of Organic Acids and Ammonia from Their Salts, Ser. No. 08/639,831, filed Apr. 29, 1996 now U.S. Pat. No. 5,814,498.

The invention includes an apparatus and its related method using an electrodialysis cell (or cells) in combination with a nanofiltration unit for filtering an incoming monovalent salt solution in order to minimize the level of multivalent impurities. The apparatus may also include an electrodialysis cell (or cells) in combination with an ion exchange column in communication with a base loop of the said electrodialysis cell. The pH of the base product from the apparatus maybe in the range of 5–14 and preferably in the range of 7 to about 13.5.

The apparatus and process are particularly well suited to the production of acids, especially organic acids, in conjunction with weak bases such as ammonia, or the salts of weak acids such as sodium carbonate or sulfite. The electrodialysis cells of the invention may employ membranes, such as bipolar membranes, or assemblies for splitting water. Alternatively the splitting of water for acid, base production may be accomplished with a set of electrodes.

BACKGROUND OF THE INVENTION

Fermentation processes for producing organic acids, such as acetic and lactic acids, go through an intermediate production of salts, such as ammonium acetate or lactate. Hence, salts are the byproducts or intermediate products of a number of chemical processes. For example, regenerable flue gas desulfurization processes use a sodium alkali to absorb the $SO_2$, thus resulting in a soluble bisulfite salt, $NaHSO_3$. Production of soda ash ($Na_2CO_3$) requires the processing of the raw material salt viz., trona ($Na_2CO_3 \cdot NaHCO_3 \cdot 2H_2O$) or the naturally occurring brines. In magnetohydrodynamic power generation process the potassium carbonate seed material absorbs $SO_2$ in the fuel and is converted to a byproduct potassium sulfate.

Electrodialysis(ED) may be used to convert these and other soluble salts directly into their acid and base components. For example, such a procedure enables a direct recovery of a relatively pure form of the organic acid from its organic salt. The co-product base (ammonia for example) may be recovered for reuse in the fermentation process for pH adjustment, thus permitting an economical and environmentally superior option for producing organic acids. In other instances, such as with sodium bisulfite, trona or potassium sulfate, the electrodialysis offers an environmentally superior route for recovering or recycling the acid, base components.

Electrodialysis uses direct current as a means for causing a movement of ions in the solutions of the processing streams of salt starting material. Electrodialysis processes are usually carried out in an arrangement comprising a stack where a plurality of flat sheet ion exchange membranes and gasket sheets are clamped together. These sheets provide flow paths for containing salt materials that produce acids and bases. The process unit requires a means for splitting water into hydrogen ($H^+$) and hydroxyl ($OH^-$) ions.

Two useful means for splitting water are:

(1) A bipolar membrane or a bipolar module formed by a combination of cation and anion membranes which functions as a bipolar membrane. Suitable bipolar membranes are available from Aqualytics, a division of Graver Water, and from Tokuyama Soda, and from the Formic Corporation; and (2) An electrode set comprising an anode and a cathode. The electrodes, particularly the anodes, are coated for chemical stability, for minimizing power consumption, and for the formation of byproducts other than hydrogen (at cathode) and oxygen (at the anode), among other things. Suitable electrodes are available from the Eltech Corporation, the Electrode Products Inc., and from others. A hydrogen depolarized anode can also generate $H^+$ ions in an aqueous solution of an electrode stream next to the anode.

As described in my above-identified co-pending applications, the stack contains electrodes (anode and cathode) at either end and a series of membranes and gaskets which have open active areas in their middle to form a multiplicity of compartments which are separated by the membranes. Usually, a separate solution (an electrode stream) is also supplied to each of the compartments containing the electrodes. Special membranes may be placed next to the electrodes to prevent a mixing of the process streams with the electrode streams.

The majority of the stack between the electrode compartments comprises a repeating series of units of different membranes with solution compartments between adjacent membranes. Each of the repeating units is called the "unit cell" or simply a "cell." The solution is supplied to the compartments by internal manifolds formed as part of the gaskets and membranes or by a combination of internal and external manifolds. The stacks can include more than one type of unit cell.

Streams of processing fluids may be fed from one stack to another in order to optimize process efficiency. After one pass through the stack, if the change in the composition of a process stream is relatively small, the process solutions can be recycled by being pumped to and from recycle tanks. An addition of fresh process solution to and withdrawal of product from the recycle loop can be made either continuously or periodically in order to maintain the concentration of products within a desired range.

When bipolar membranes are used to form acid or base from the salt, in order for the membrane to function as a water splitter, the component ion exchange layers must be arranged so that the anion selective layer of each membrane is closer to the anode than the cation selective layer. A direct current passed through the membranes in this configuration causes water splitting with OH⁻ ions being produced on the anode side and a corresponding number of H⁺ ions being produced on the cathode side of the membranes. The dissociated salt anions move toward the anode. The dissociated salt cations move toward the cathode.

The electrolysis process works in a similar manner, with the water splitting occurring at the two electrodes. When a direct current appears, water molecules are converted to oxygen gas at the anode along with the introduction of H⁺ ions into the aqueous solution. At the cathode, the water molecules are converted to hydrogen gas along with the introduction of OH⁻ ions into the aqueous solution. In the hydrogen depolarized anode based electrolysis unit, OH⁻ ions are released into the aqueous solution next to the cathode. While released, the hydrogen gas is forwarded to the catalytic hydrogen depolarized anode for H⁺ ion generation.

Electrodialysis equipment for acid/base production may have three compartment cells comprising bipolar, cation and anion membranes; two compartment cells containing bipolar and cation (or anion) membranes; multichamber two compartment electrodialysis cells comprising bipolar and two or more cation membranes. The term "bipolar membrane" also includes bipolar equivalent structures, such as the use of electrodes and composite bipolars. FIG. 1 shows the unit cell for the three most useful configurations.

Specific references are:
"Electrodialysis Water Splitting Technology" by K. N. Mani; J. Membrane Sci., (1991), 58, 117–138
U.S. Pat. Nos. 4,082,835; 4,107,015; 4,592,817; 4,636,289; 4,584,077; 4,390,402; and 4,536,269.

In accordance with an aspect of this invention, an electrodialysis apparatus is improved through the addition of a nanofiltration unit upstream of an electrodialysis cell or through the use of a downstream ion exchange column in combination with the electrodialysis cell and in communication with the base loop of the cell. Or both nanofiltration and an ion exchange column may be used.

In another aspect of the invention, the use of monovalent selective cation membranes in combination with adequate dilution of the base product allows reliable non-fouling operation of the electrodialysis cell to produce acid and base from salt.

BRIEF DESCRIPTION OF THE DRAWINGS

The invention may be understood best by reading the following specification in connection with the attached drawings, in which:

FIGS. 1(a)–1(c) schematically show construction of the unit cells for two and three compartment electrodialysis cells using bipolar membranes;

CELL CONSTRUCTION

Figure 2A:
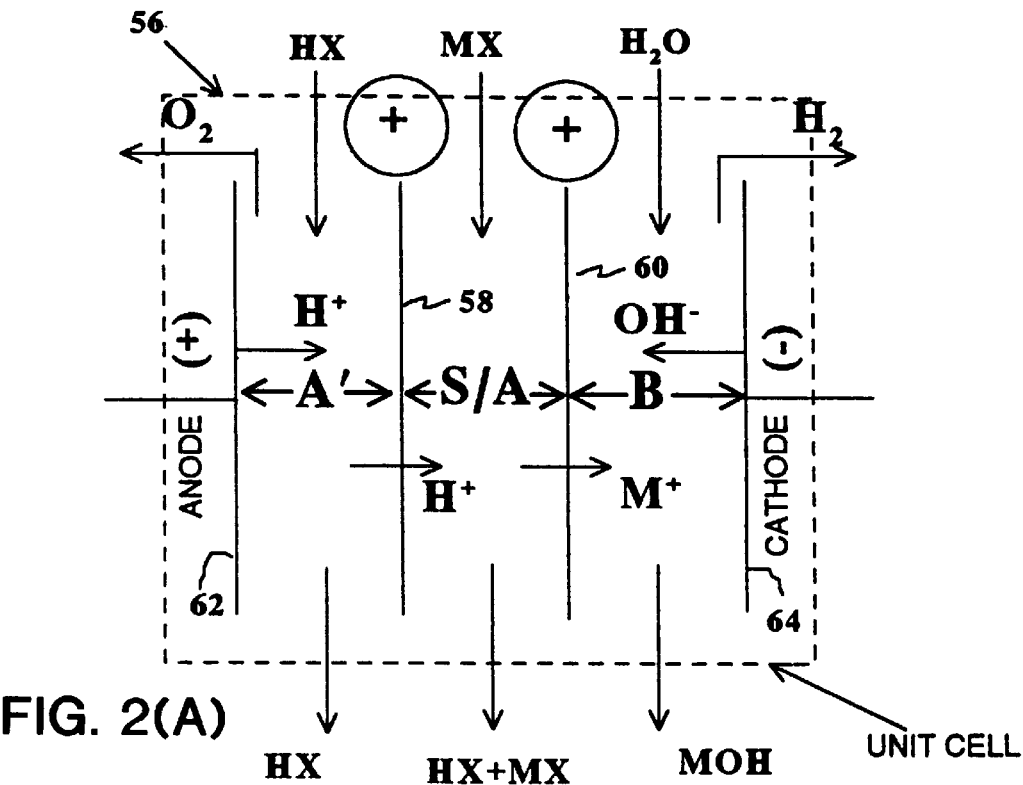
FIGS. 2(a), 2(b) schematically show construction of the unit cells for two and three cells using a set of electrodes.

FIG. 1(a) shows a two compartment cell 20 comprising bipolar (designated as −+) membranes 22, 23 and anion (designated as −) membranes 24, 26. A salt/base compartment (S/B) is located between the anion surface of the bipolar membrane 22 and the anion membrane 24. An acid compartment (A) is located between the cation surface of the bipolar membrane 22 and another anion membrane 26. The combination of these two compartments (S/B and A) and of the membranes 22–26 is termed a "unit cell" or, simply, a "cell." Then, the cell compartments repeat, as at S/B'; and continuing on. As many as two hundred or more such cells may be assembled between an anode (+) 28 and a cathode (−) 30.

The salt solution 32 process feedstream which is to be acidified, a lactate solution MX, for example, is fed into the salt/base compartment S/B, while a liquid comprising water 34 may be supplied to the acid compartment. Under a direct current driving force, the bipolar membrane 22 splits the water, generating H⁺ and OH⁻ ions as shown (FIG. 1(a)). Simultaneously, the X anions resulting from the dissociation of the salt stream MX are transported across the anion membrane to the acid compartment, where they combine with the H⁺ ions to form the acid HX. The process may be represented schematically as follows:

(Salt/base compartments) MX+OH⁻−X⁻=MOH

(Acid compartments) H⁺+X⁻=HX.

The process has been detailed fully in my earlier co-pending patent applications. This process is best suited for processing salts of weak bases, particularly for processing ammonium salts. The concentration of the acid product that can be made is in the order of 1–6 N, with the higher concentrations being feasible for weak organic acids (PK$_a$ of about 2.5 or greater). The feed salt concurrently becomes alkaline; with the pH being about 10–11 for ammonia production.

FIG. 1(b) shows a two compartment cell 36 comprising bipolar and cation membranes (designated as +). A base compartment (B) is located between the anion surface 38 of the bipolar membrane and the cation membrane 39. A salt/acid compartment (S/A) located between the cation surface 40 of the bipolar membrane and another cation membrane 42. The combination of the two membranes and the two compartments is termed a "cell." Two hundred or more such cells may be assembled between an anode and a cathode.

The salt solution to be acidified (an organic salt solution MX, for example) is fed to the salt/acid compartment S/A, while a liquid comprising water may be supplied to the base compartment B. Under a direct current driving force the bipolar membrane generates H$^+$ and OH$^-$ ions as shown in FIG. 1(b). Simultaneously the M$^+$ cations resulting from the dissociation of the salt MX are transported across the cation membrane to the base compartment, where they combine with the OH$^-$ to form the base MOH. The process may be represented as:

(Salt/Acid compartments) $MX+H^+-M^+=HX$ (Base compartments) $M^++OH^-=MOH$

The conversion of the salt that can be carried out efficiently by this arrangement is determined by the amount of current used (coulombs), the concentration of the salt solution and, importantly, by the pK$_a$ of the acid involved. For weakly dissociated acids with a pK$_a$ greater than about 2.5 the conversion can be from about 80% to about 97%. Most organic acids such as lactic, acetic, citric, formic and other acids fit into this category. The residual cation content in the acid product can then be removed, if necessary, via a conventional cation exchange resin.

FIG. 1(c) shows a three compartment cell 44 using bipolar 46, cation 48 and anion 50 membranes. Three compartments, acid(A), base(B) and salt(S) are located between these three membranes, as shown. The entire combination of membranes and compartments is termed a "cell." As with the two compartment cells of FIG. 1(b), many cells may be placed between a single set of electrodes. This three compartment cell arrangement is the most generic for the production of acids and bases, particularly strong acids, such as hydrochloric and nitric acids, and strong bases such as sodium hydroxide and potassium hydroxide.

The salt solution is fed into the S compartment located between the cation 48 and anion 50 membranes. A liquid comprising water is fed to the acid and base compartments located on either side of the bipolar membrane. Under a direct current driving force the H$^+$ and OH$^-$ ions generated at the bipolar membrane 46 are transported to the acid A and base B compartments, respectively. Concurrently, the M$^+$ ions are transported across the cation membrane 48 to the base compartment B, while the X$^-$ ions are transported across the anion membrane 50 to the acid compartment A. The net effect is the production of relatively pure acid (HX) and base (MOH) products from the salt MX.

Other cell arrangements involving bipolar membranes in conjunction with two or more cation membranes or two or more anion membranes may also be used in processing salts where the pK of the product acid or base is in the intermediate range. Such cell arrangements convert the salt to an acid and a base at a higher current efficiency, as compared to the conversion of the two-compartment cells shown in FIGS. 1(a) and 1(b), but it is also at higher capital and operating costs.

The operation of the process using electrodes as the source of H$^+$ and OH$^-$ ions is often termed electrolysis which involves the co-production of O$_2$ and H$_2$ at the anode and cathode, respectively. Electrolysis operation is similar to the operation of the bipolar membrane electrodialysis described above. The main difference between these two operations is the membranes which appear between an anode and a cathode. With each cell containing a set of electrodes, a number of cells may be assembled into a single process unit. The electrical and hydraulic connections between the cells may be made in either a series or a parallel combination in order to form a compact commercial process unit. Exemplary references are:

Meliere, K. A., et. al., "Description and Operation of Stone & Webster/Ionics SO$_2$ removal and recovery" U.S. NTIS Report, PB-242 573, (1974), 1109–26.

U.S. Pat. No. 3,475,122.

Figure 2B:
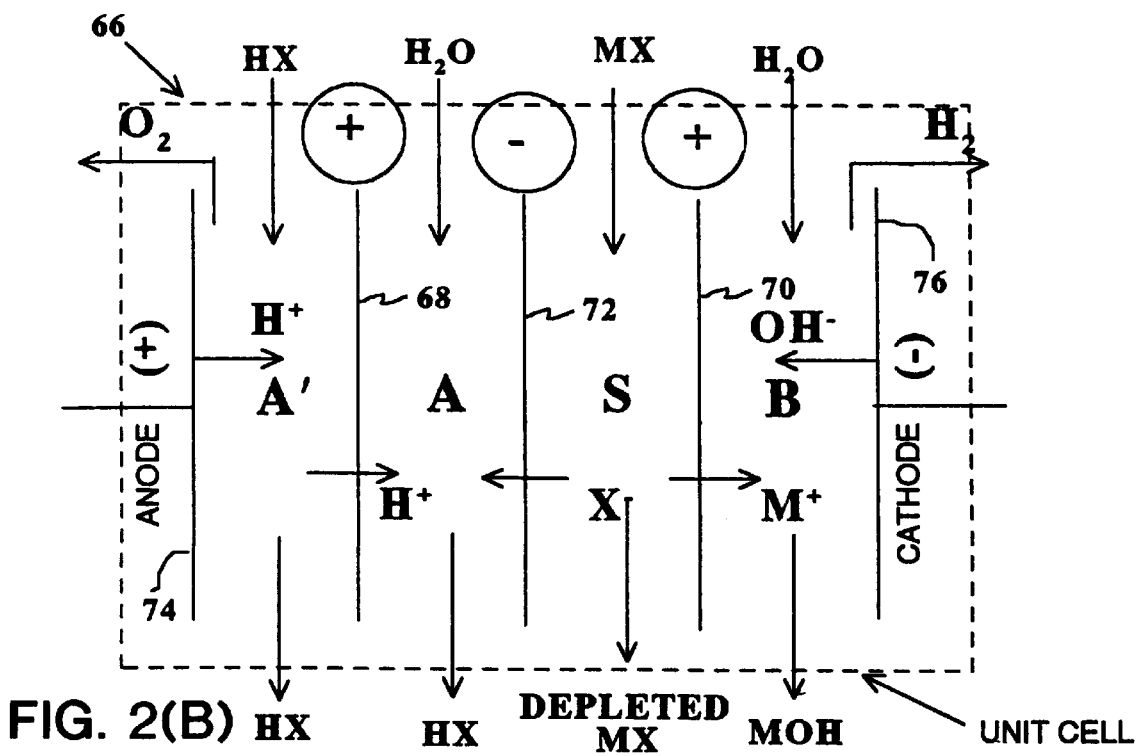

FIGS. 2(a)–2(b) show two of the possible cell arrangements. More particularly, FIG. 2(a) shows a cell 56 using two cation membranes 58, 60 and three compartments located between an anode (+) and a cathode (−). The operation of the process is similar to the operation of the two-compartment cation cell shown in FIG. 1(b) and is particularly applicable to the production of weak acids from their salts. A separate acidic stream may be circulated in the compartment A' which is a buffer compartment next to the anode 62. The salt process stream which is to be processed is circulated in the compartment between the two cation membranes 58, 60. The buffer compartment A' and cation membrane 60 are used to contain the salt stream. While the buffer compartment is preferred, it is not essential to the operation of the two compartment cell.

A stream comprising water is circulated in the B compartment next to the cathode 64. Under a direct current driving force, H$^+$ and OH$^-$ ions are generated at the anode and cathode, respectively, along with oxygen and hydrogen which are co-products from the dissociation of water. Simultaneously, the H$^+$ ions are transported across the first cation membrane 58 to the intermediate salt/acid (S/A) compartment where it combines with the anion X$^-$ to form the acid HX. The M$^+$ cation is transported across the second cation membrane 60 to the B compartment to form the base MOH.

The reactions may be summarized as follows:

| | |
|---|---|
| (Buffer A' compartment) (H$^+$ transported out across the first cation membrane) | $H_2O = \frac{1}{2}O_2\uparrow + 2H^+ + 2e^-$ |
| (Salt/acid compartment) | $2MX + 2H^+ - 2M^+ = 2HX$ |
| (Base compartment) | $2H_2O + 2e^- = 2OH^- + H_2\uparrow$ |
| | $2M^+ + 2OH^- = 2MOH$ |
| (Overall) | $2MX + 3H_2O = 2HX + 2MOH + H_2\uparrow + \frac{1}{2}O_2\uparrow$ |

FIG. 2(b) shows another version of a four compartment cell 66 using two cation membranes 68, 70 and one anion membrane 72 between an anode 74 and a cathode 76. The operation of this cell 66 is similar to the operation of the three compartment cell shown in FIG. 1(c). The cell 66 is capable of generating relatively pure acid and base. The salt MX is fed to the compartment S between the anion membrane 72 and the second cation membrane 70. The anion membrane separates the acid product from the feed salt. Otherwise, the operation of the cell is similar to the operation of the two-compartment cell shown in FIG. 2(a).

When cells 56, 66 of FIGS. 2a, 2b are compared with the bipolar membrane based cells 20, 36, 44 (FIGS. 1(a)–1(c)), the co-production of hydrogen and oxygen at the electrodes along with the acid and base products requires an additional energy input to the process of about 1.2V/cell. One option that can reduce this power load is the use of a hydrogen depolarized anode in place of a conventional anode.

Figure 3:
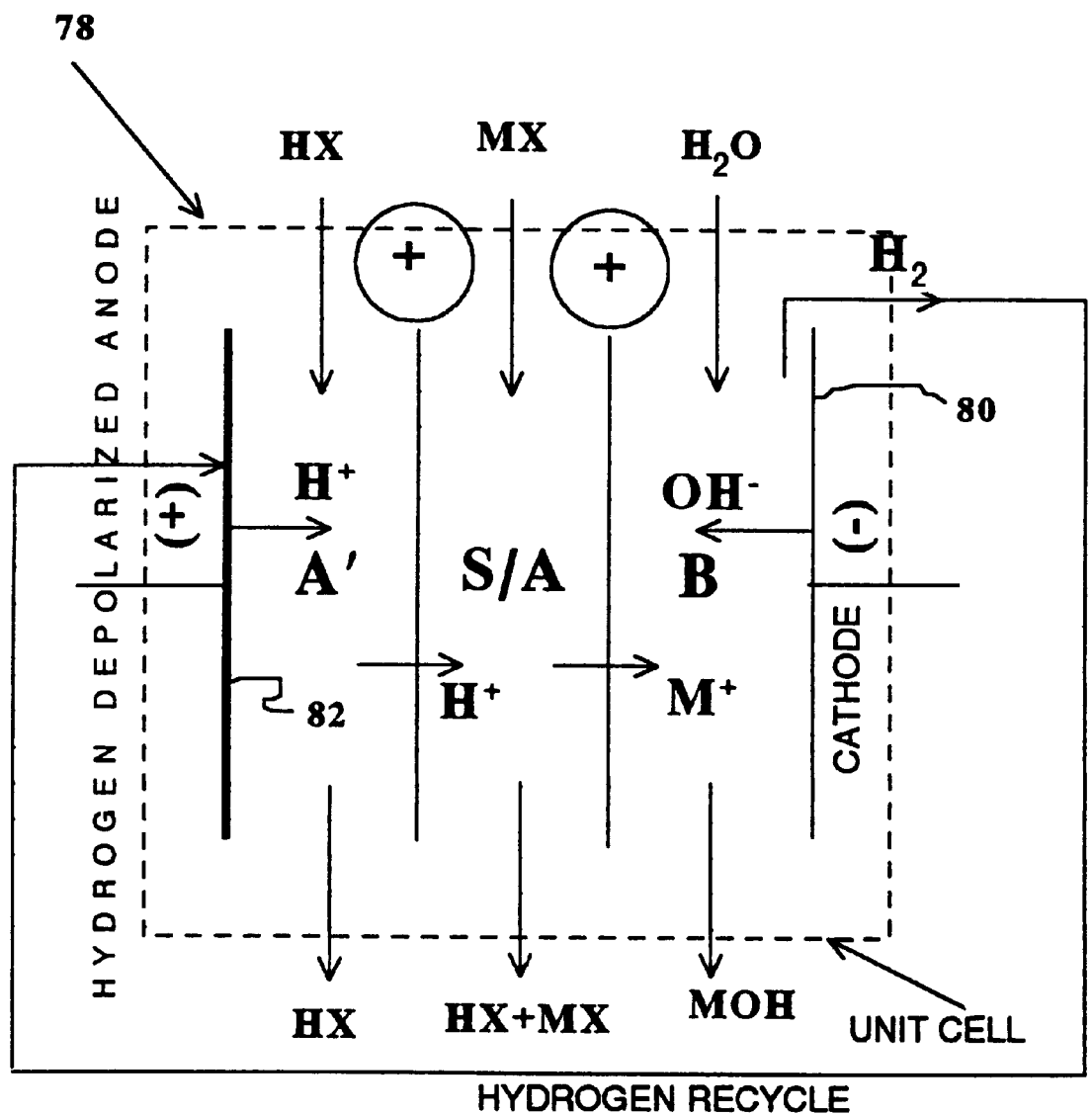
FIG. 3 schematically shows a two compartment cell using a hydrogen depolarizing electrode.

FIG. 3 shows the construction of a cell 78 with a hydrogen depolarized anode, which is conceptually identical to cell 56 of FIG. 2(a). In such a cell, the hydrogen gas produced at the cathode 80 is returned to the anode 82 where it is oxidized to protons at a gas diffusion electrode. The $H^+$ ions are released into the aqueous solution next to the gas diffusion electrode 82. This technique can lower the cell voltage by about 1 volt/cell, thus reducing the power consumption level to be somewhat nearer to that obtained with a cell using a bipolar membrane. (Membrane & Separation Technology News, (1996), 15(2), 2–4). Other cell configurations employing the gas diffusion anodes can be visualized by those skilled in the art.

For purposes of this disclosure, the cells employ bipolar membranes, a combination of cation and anion membranes that behave together as a bipolar membrane. The cells may also employ bipolar membrane equivalents, such as structures using electrodes and composite bipolars. The cells that have a set of electrodes generating $H^+$ and $OH_-$ ions, a hydrogen depolarized anode based cell that collects the hydrogen gas at the cathode and injects it into the companion porous catalytic electrode to generate $H^+$, may be considered equivalent. The term "bipolar membrane" or its equivalent will be used herein to denote any one of these options.

Despite the usual filtration/ultrafiltration and carbon treatment steps, a major problem in using the electrodialysis cells in the water splitting applications, is that the feed salt contains a significant amount of divalent metal ions, particularly calcium and magnesium. When the feed stream is processed, the metal ions are transported to the base loop of the electrodialysis unit. Due to their poor solubility, the metal ions are precipitated in the base loop. The precipitation of these ions inside the base loop plugs the cells, and damages the membranes thereby decreasing the current throughput and, in the extreme, causing a mechanical failure resulting from an overheating and, perhaps, a meltdown.

A resin based ion exchange is a standard technique used to reduce the calcium and magnesium levels in the feed stream to the low levels required for the proper operation of the electrodialysis cells. A problem with this approach is that the pH of the feed stream has to be raised to >9 through an addition of a base material. The feed stream is filtered one more time (to remove any precipitates formed) in order for the ion exchange step to be effective. Such a step is practiced, for example, in the purification of NaCl streams in the production of caustic soda via electrolysis.

Many of the salts from the commercially important processes are acid or neutral. These salts may result from a fermentation of dextrose to organic acids—e.g. lactic, citric, acetic, 2-keto gulonic, and the like. These salts have a pH range of 4 to 7 and contain significant amounts of free acids as well as calcium or magnesium which had been added as nutrients during the fermentation step. Such salt solutions require an addition of considerable quantities of alkali in order to raise the pH to a point where an effective operation of the ion exchange column can be assured. The added base would then have to be recovered in the electrodialysis unit at an added cost in terms of the capital cost of the membrane area and electrical power consumption.

Another application where acidic salt is produced is in flue gas desulfurization. In the process, the sulfur dioxide in the flue gas is absorbed in a solution of sodium sulfite (pH of 9.5–11) resulting in an acidic salt solution of sodium bisulfite (pH 4–5.5). The bisulfite stream can then be processed in the electrodialysis units to recover the $SO_2$ product and the alkali which may be recycled to the absorber. (U.S. Pat. Nos. 3,475,122; 4,082,835). However, a problem is that the flue gas, which is derived from the combustion of fossil fuels, contains flyash derived impurities, usually including calcium and magnesium compounds and, possibly, corrosion products (iron) from the duct work through which the flue gas passes. The presence of these impurities make the processing of the bisulfite stream in the water splitter rather difficult, if not impossible.

A similar situation exists in the processing of impure alkaline sodium brine streams used to make sodium carbonate or sodium hydroxide. The brine stream may be from certain surface sources (such as Searles Lake in California) or from a mineral source such as trona (sodium sesquicarbonate), derived via mining at Green River, Wyo. In a water splitting process the mineral is acidified to liberate carbon dioxide in the acid loop. Depending on the process choice, the acidified product may be reacted with an additional sodium mineral either in an above ground reactor or in an under ground mine (solution mining) to liberate $CO_2$ and a neutral sodium salt (e.g. sodium sulfate).

Concurrently, in the base loop, sodium carbonate is produced by reacting the caustic soda product with a portion of the bicarbonate feed or by absorbing the carbon dioxide in the sodium hydroxide generated in the base loop. U.S. Pat. Nos. 4,584,077, 4,592,817 and 4,636,28 contain examples of such processes. In addition to containing quantities of sodium sulfate, sodium bicarbonate, sodium chloride, and sodium carbonate, the minerals also contain, among other things, some calcium and magnesium compounds which could hamper their direct processing via electrodialysis.

In the above described and other similar applications, it would be highly desirable to have improved apparatuses and processes that can treat an acidic or near-neutral pH salt to yield the corresponding acid and an alkali at a pH of 9–14, without the need for an upstream pH adjustment and ion-exchange.

An earlier of my co-pending patent applications, Ser. No: 08/639,831 now U.S. Pat. No. 5,814,498 discloses a use of a nanofiltration step to reduce the calcium and magnesium levels in solutions containing ammonium salts of monovalent organic acids. Subsequently, such solutions are processed in a two compartment electrodialysis cell containing bipolar and anion membranes. This process generates an ammoniacal organic salt solution at a pH of about 10 and a concentrated solution of the organic acid. While effective in reducing or eliminating the precipitate formation at the bipolar membrane surface, the co-pending application does not address either the production of concentrated alkaline solutions or the production of multivalent acids.

A need exists for superior apparatuses for producing concentrated alkaline streams, e.g., ammonia, sodium sulfite, sodium carbonate, sodium hydroxide and other materials in the pH range of 9–14 and for processes which produce such streams.

Another need exists for an improved process that can convert salt solutions without the need for either pH adjustment or an upstream ion exchange resin based softening step, while achieving a reliable long term operation of the electrodialysis cell and the production of concentrated alkaline solutions.

Yet, another need also exists for a process that can concurrently generate relatively pure acid co-products.

Still another need also exists for a novel apparatus and process that can directly process filtered/ultrafiltered solutions of ammonium or alkali metal salts of organic or inorganic acids to yield a concentrated ammonia or alkali, while yielding a relatively pure acid or a substantially acidified salt stream.

SUMMARY OF THE INVENTION

The invention provides improved apparatuses, methods, and processes for converting a variety of salt streams into relatively pure acids and alkaline products. The alkaline product may be almost any pH, but for many applications the pH is preferably in the range of 7 to about 13.5. The invention grew out of a number of findings: (a) When processing salts of certain organic acids, the multivalent cations apparently bind with the organic anion. This substantially reduces their transport out of the salt or the salt/acid solution. (b) With the appropriate cation membranes and when dealing with weak acids, a portion of the divalent metal cations may be retained in the feed salt loop. The balance of these cations are transported to the base loop without causing a fouling of the cation membranes. (c) The transported divalent metals have a low but finite solubility in the alkaline product solution.

By devising suitable apparatuses that can attain and maintain a sufficiently low concentration of the divalent metals in the base loop, the precipitation of these metals either does not occur or is not a serious problem. Maintaining low concentrations of the divalent metals in the base loop, thereby averting their precipitation, has surprisingly beneficial effects such as a high and steady current throughput and the elimination of shunt and stray currents related heating and melting problems. Long term trouble-free operation of the electrodialysis cell hardware, membranes and the process are thereby achieved.

One aspect of the invention resides in processing salts of weak, low molecular weight monovalent acids. In this, the feed solution (e.g., ammonium lactate or acetate) is subjected to nanofiltration. The nanofilter that is most effective has a rating in the order of about 200 Daltons. Thus, the molecular weight of the acid that can be efficiently processed is less than about 150 Daltons. The feed may be at almost any pH, but preferably is in the range of 4–10. The nanofiltration step produces a filtrate wherein the divalent metals content in the salt stream is less than approximately 25 ppm total.

The purified salt stream is then processed in a two compartment cell containing bipolar membranes (or their equivalent) and cation membranes. The feed salt stream is fed to the salt/acid compartment contained between the cation side of the bipolar membrane and the cation selective membrane while a stream of water is fed into the base compartment between the cation membrane and the anion side of the bipolar membrane. Under a direct current driving force, the feed salt is acidified in the cell to the extent that is technically and economically feasible as a result of the $H^+$ ions generated by the bipolar membrane.

Concurrently, the salt cation is transported to the base loop where it combines with the $OH^-$ ions generated by the bipolar membrane to form the base product. The extent of the conversion of the salt to an acid in the acid loop is determined primarily by the amount of current (coulombs) passed through and by the $pK_a$ of the acid. For weak acids having $pK_a$'s greater than ~2.5, there is a conversion of 80–97%. Many organic acids fit this category.

This invention can be used for base products in the pH range of 5–14, preferably in the range of 7–13.5, and more preferably in the pH range of 8–11. When the feed stream contains an additional salt of a stronger acid with the same cation (e.g. ammonium lactate and ammonium sulfate), the additional salt becomes a supporting electrolyte. The formal conversion of the weak acid can be in the order of 100%. Some times, other parts of the system may contain weak acid which was not part of this original feed, in which case the weak acid conversion may be greater than 100% of the weak acid in the feed. The product acid then may have some excess $H^+$ ions. The product base is typically at a strength of 1–5 N.

A second aspect of the invention is subjecting the salt of the monovalent acid (molecular weight less than approximately 150) to nanofiltration, followed by processing in a three compartment cell which contains a bipolar membrane (or its equivalent), cation membranes and anion membranes. After nanofiltration in order to reduce its multivalent cation content to below about 25 ppm, the feed salt solution may be at any pH (preferably in the range of 4–10). The solution is fed into a salt compartment contained between cation and anion membranes. Liquids containing water are fed to the acid and base compartments. The acid compartment is contained between the cation side of the bipolar membrane and the anion membrane. The base compartment is contained between the anion side of the bipolar membrane and the cation membrane. The feed solution is depleted of its salt content in the process, while a relatively pure product acid and base at concentrations at 1–5 N strength are generated.

The invention can be used to generate base products in the pH range of 5–14, preferably in the pH range of 7–13.5, and more preferably in the pH range of 8–11. In contrast with the two-compartment version, the three-compartment cell can be used for producing strong or weak low molecular weight monovalent acids.

Another aspect of the invention is a novel apparatus and process that incorporates an ion exchange column in communication with the base loop of the electrodialysis cell. The feed salt solution, which may be at any pH, but typically in the range of about 4–10, is suitably filtered to remove insoluble matter and then processed in an electrodialysis cell containing bipolar membranes or their equivalent.

The base compartment of the cell, contained between the anion side of the bipolar membrane and the adjacent monopolar membrane, is connected to an ion exchange column. The base solution circulates through both the cell and the column. The ion exchange column contains an ion exchange resin capable of removing substantially all of the multivalent metal ions that may enter the loop, either across the cation membrane or from the aqueous feed solution to the loop. The base product may be at any pH in the range (5–14), particularly when the base loop is contained between a cation membrane and the anion side of the bipolar membrane. For an efficient removal of the multivalent cations, (particularly calcium and magnesium), the pH in the base loop is preferably in the range of about 7–14; and most preferably about 8–11.

The electrodialysis cell may be of the two-compartment type, comprising bipolar membranes and either cation or anion membranes, or a three compartment cell containing bipolar, cation and anion membranes. Multichamber cells containing two or more monopolar membranes of the same type as detailed in U.S. Pat. Nos. 4,536,269; 4,608,141 may also used as part of the improved process and apparatus.

The inventive process and apparatus has been found to be particularly efficient when the base compartment of the electrodialysis cell is contained between the cation membrane and the anion surface of the bipolar membrane. This arrangement is used because additional separation and retention for the multivalent metals are provided by the cation membranes which reduces the amount of these metals in the base loop, thereby saving on the cost of isolating them. Consequently the ion exchange load for these species may be substantially reduced and the ion exchange column can be made substantially smaller in relation to the amount of multivalent cations in the feed stream being processed.

In another aspect of this invention, the feed salt solution has relatively low levels of hardness or can be purified via conventional pH adjustment filtration steps in order to reduce the total hardness to their solubility levels. This version also has the advantage that it can process salts of mono- or multivalent acids. In ammonium lactate production via fermentation, for example, the amount of nutrients can be carefully controlled so that ammonium lactate solution obtained after the usual cell removal and ultrafiltration steps may have for example <50 ppm Ca and <25 ppm Mg. With sodium chloride or sodium sulfate solutions the typical concentrations of Ca, Mg in the purified solutions are <10 ppm and <1 ppm respectively. Such solutions can then be processed in electrodialysis cells containing the monovalent selective or monovalent favoring cation membranes to generate acid and base. Sufficient dilution water is added to the base loop in these instances in order to maintain the concentration of the divalent metals below their solubility limits and as a result an ion exchange column is not needed in the base loop.

This novel apparatus may be used for processing a variety of salts of monovalent cations, such as ammonium, sodium and potassium. The anion of the salt may be monovalent or multivalent, (e.g., halides organic anions, bisulfite, sulfate, phosphate, or mixtures thereof), the main constraint being that the salts be fairly soluble in water.

DETAILED DESCRIPTION OF THE VARIOUS EMBODIMENTS

In accordance with this invention, an electrodialysis apparatus is improved through incorporation of a monovalent selective cation membrane, the addition of a nanofiltration unit upstream of an electrodialysis cell or through the use of an ion exchange column in combination with the electrodialysis cell and in communication with the base loop of the cell.

Figure 4A:
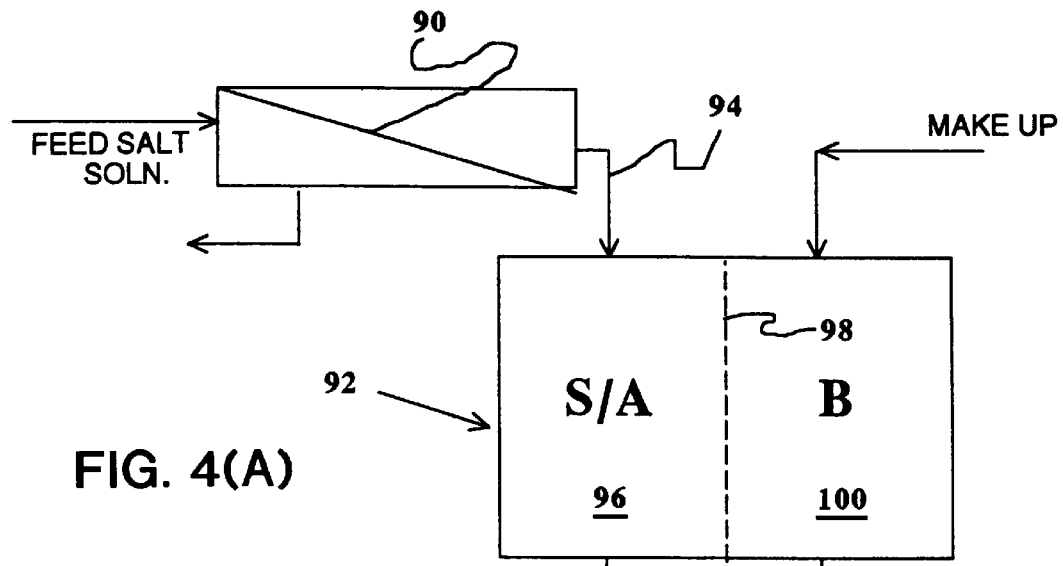
FIGS. 4(a) and 4(b) are block diagrams which show the invention using an electrodialysis system having an upstream nanofiltration.
Figure 4B:
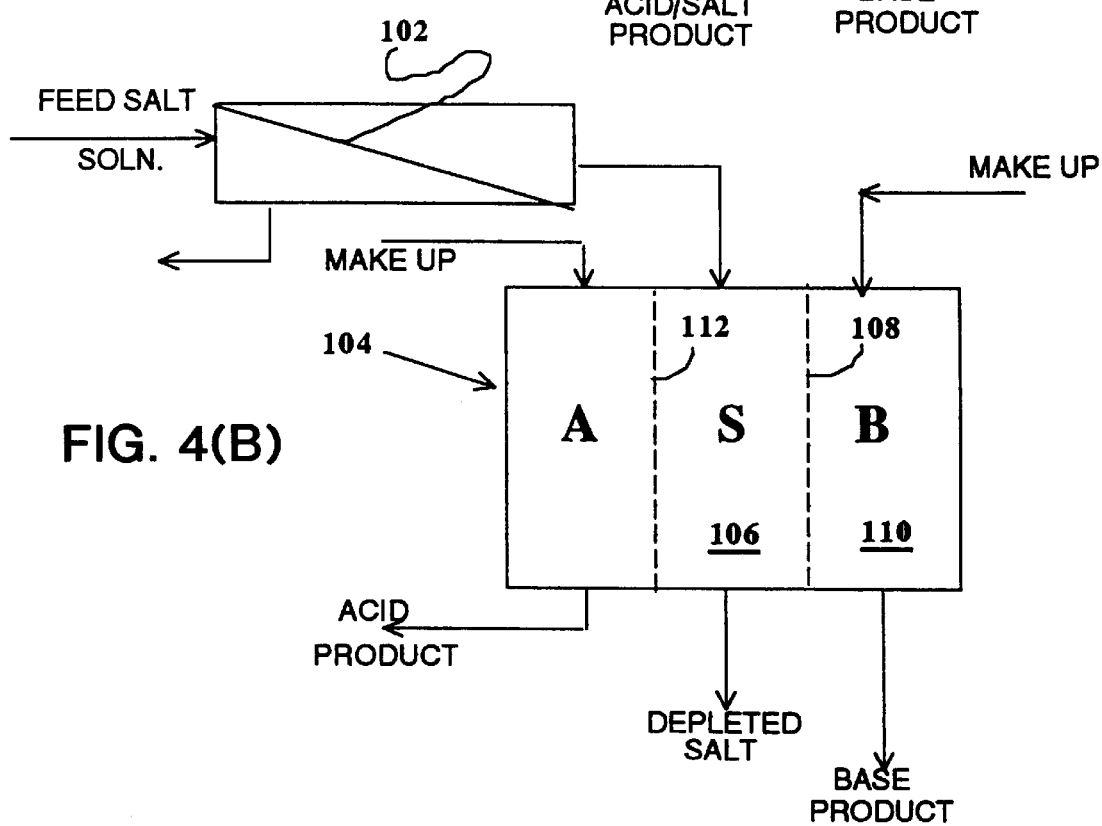

The improved apparatuses can be better understood from FIGS. 4(a)–4(b), 5(a)–5(c). Other kinds of cells or cell designs can be visualized by persons skilled in the art. FIGS. 4(a) and 4(b) show the apparatus of this invention that uses a nanofilter in conjunction with an electrodialysis units such as is shown in FIGS. 1–3.

FIG. 4(a) shows a nanofilter 90 operating upstream of a two-compartment cation cell 92. The cell may of the type shown in or similar to FIGS. 1(b), 2(a), 3, or which may employ two or more cation membranes. The nanofilter has a typical molecular weight cut off of about 200. Suitable filters are available from Desalination Systems, Filmtec and others.

The feed stream may be a salt of a monovalent cation and -monovalent anion, may be at almost any pH, but usually is at a pH of 4 to 10. The feed stream may contain multivalent cation impurities and is initially processed in the nanofiltration unit containing filter 90 to obtain a filtrate with a divalent metal content of about 25 ppm total. The filtered stream is fed through pipe 94 to the salt/acid compartment 96 of the cell 92. When processing salts of low molecular weight (i.e. less than about 150) weak acids, this reduced level of multivalent cations has been found to be adequate for ensuring a long term, trouble-free operation of the electrodialysis cell.

The nanofiltered feed stream in the salt/acid (S/A) compartment 96 of the two compartment cell 92, is usually a weak acid such as lactic, acetic, formic and the like, and is acidified by the protons generated by the bipolar membrane (or its equivalent). The salt cation $M^+$ is transported across the cation membrane 98 to base compartment 100. The pH of the base is produced by the input of $OH^-$ ions from a bipolar membrane in the base (B) compartment 96. The pH of the base is controlled to be in the range of about 5–14 and preferably in the pH range of 7–13.5 in order to ensure a trouble-free operation of the electrodialysis cell. The latter pH range is naturally achieved when a weak base, such as ammonia, is produced.

Alternatively, the pH may be kept within a target range by an addition of a neutralizing compound, such as $CO_2$, sodium bicarbonate($NaHCO_3$), sodium bisulfite($NaHSO_3$) or $SO_2$. The resulting basic salt is a marketable product (as is the case with sodium carbonate) or a reusable chemical (such as sodium sulfite, $Na_2SO_3$ for use in flue gas scrubbing, for example).

As opposed to the use of nanofiltration in conjunction with the two-compartment anion cell disclosed in my earlier co-pending Application (Ser. No. 08/639,831), the apparatus of FIG. 4(a) has a significant advantage. With certain cation membranes, the monovalent cations are transported more effectively over multivalent cations, even at the high current densities in the order of 70–100A/ft². The cation membranes so-called monovalent favoring or monovalent selective type are not readily fouled by the multivalent cations over a broad pH range. The apparatus of FIG. 4(a) takes advantage of this phenomenon to further reduce the multivalent ion concentration in the base loop of the electrodialysis cell, thereby ensuring that they do not precipitate in the loop.

FIG. 4(b) shows another version of the apparatus, comprising a nanofilter 102 and a three compartment electrodialysis cell 104. The salt feed stream of the low molecular weight monovalent acid and a monovalent base is processed in the nanofilter and then supplied to the salt loop 106 (S) of the cell. Once again, the nanofilter is able to reduce the multivalent cation content of the feed to about 25 ppm. As with the two-compartment cation apparatus 92 of FIG. 4(a), the cation membrane 108 in the three compartment cell reduces the multivalent cation transport to the base loop 110, thereby further improving the long term reliability of the process. However, in contrast with the two compartment cation cell 92, the three compartment apparatus 104 has an extra anion membrane 112 to isolate the acid generated in the process. The three compartment apparatus 104 is capable of processing salts of strong or weak acids, while producing a relatively pure acid product. Feed streams containing salts of weak and strong acids can also be processed via this route. Once again the pH of the base product may be in the range of 5–14, but is preferably controlled to be in the range of 7–13.5 for many applications in order to ensure trouble-free operation of the electrodialysis cell.

Figure 5A:
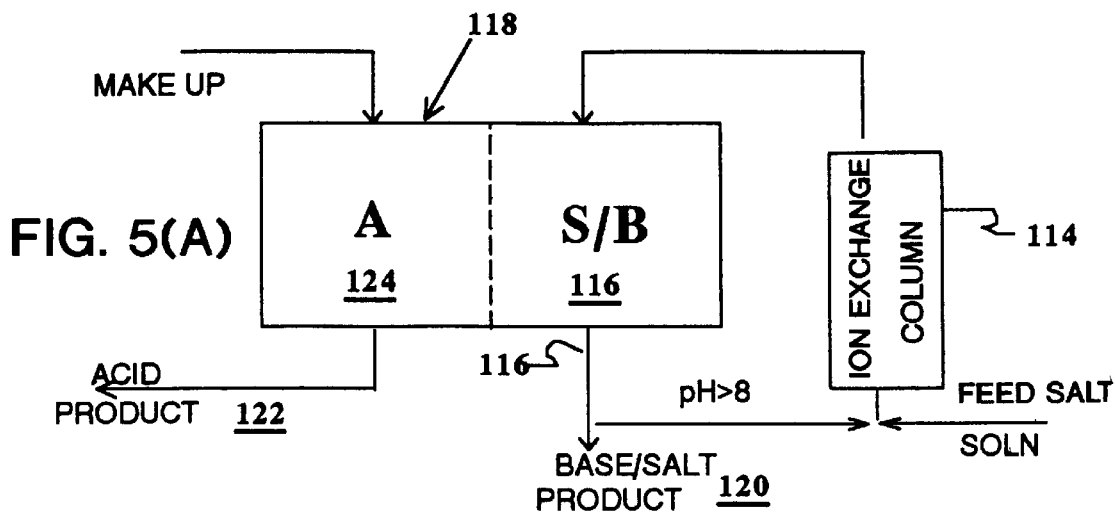
FIGS. 5(a)–5(c) are block diagrams which show another apparatus of this invention comprising an electrodialysis cell in combination with an ion exchange column in communication with the base loop of the electrodialysis cell.
Figure 5B:
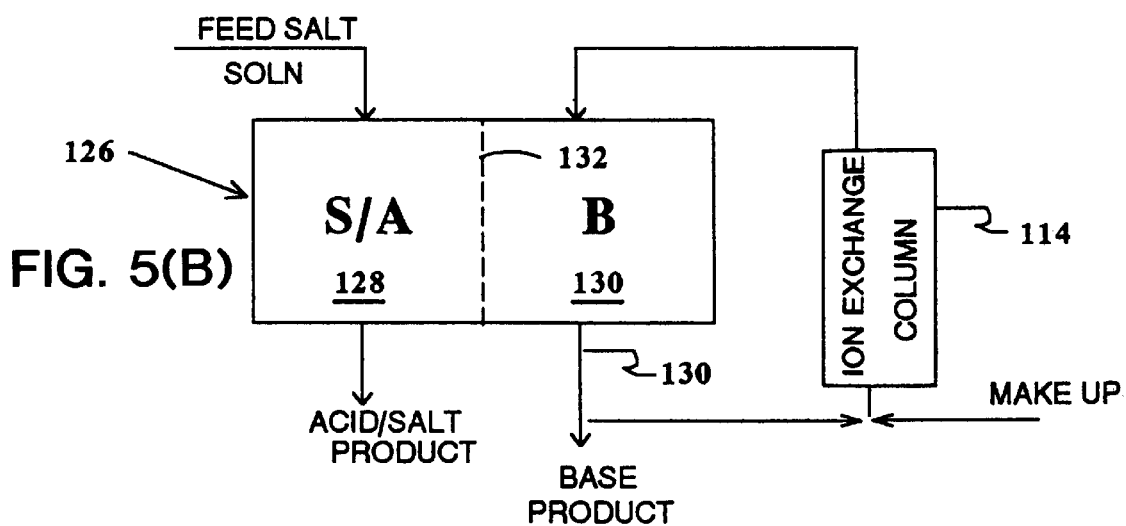
Figure 5C:
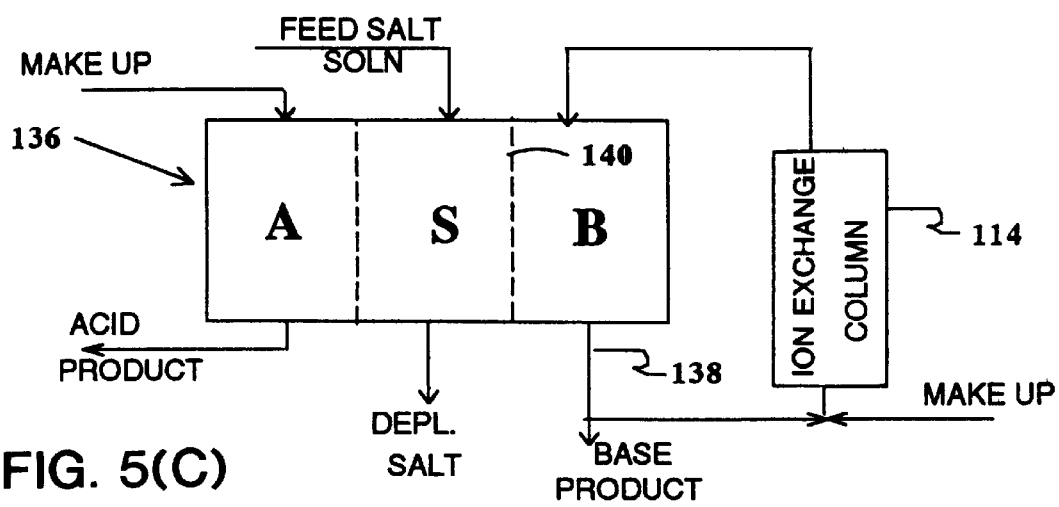

FIGS. 5(a)–5(c) show another inventive apparatus that uses an ion exchange column 114 in communication with the base loop of the electrodialysis cell. This apparatus has an advantage because it can process salts of multivalent acids.

The ion exchange column 114 contains a cation exchange resin capable of removing the multivalent ions, and particularly the divalent ions, from the base loop solution. Since the ion exchange column can in principle maintain very low levels of multivalent (mostly divalent: Ca and Mg) cations in the base loop, the pH of the generated base product can cover the entire neutral gamut, i.e. pH 7–14. With a proper ion exchange column operation, dilute solutions (0–15 wt %) of a strong base, (e.g. sodium or potassium hydroxide), can be produced. In this pH range, a weak acid cation exchange resin is particularly desirable and effective, but strong acid or chelating type cation resins may also be used. In one preferred mode, the pH in the base loop is maintained in the 7–13.5 range so as to provide a certain solubility buffer for the divalent cations. It is desirable, but not necessary, that the ion exchange resin be in the appropriate monovalent cation form prior to use in the processing operation.

Three versions of the apparatus using an ion exchange column are shown in FIGS. 5(a)–5(c). Other versions may be easily visualized by persons skilled in the art.

FIG. 5(a) shows the ion exchange column 114 in communication with the salt/base loop 116 of a two-compartment anion cell 118. This loop is preferably operated in a feed and bleed mode so that the pH in the loop is maintained at the >7 level which is needed for an efficient operation of the ion exchange column. A feed stream of a salt solution is fed to the salt/base(S/B) loop 116. The product base is withdrawn at 120, so as to achieve a requisite conversion of the feed salt. The product acid 122 is withdrawn from the acid (A) loop 124.

The ion exchange column 114 maintains the multivalent cation concentration in the base loop 116 at a level that is low enough to obtain long term trouble-free operation of the process. When the ion exchange column has been sufficiently loaded with the multivalent cation species, particularly $Ca^{+2}$ and $Mg^{+2}$, the column is taken out of the salt/base recycle loop and is regenerated with acid in the conventional manner, and then put back into service. The apparatus of FIG. 5(a) is best suited for processing salts of weak bases, such as ammonium nitrate or ammonium lactate.

FIG. 5(b) shows the ion exchange column 114 in conjunction with a two-compartment cation cell 126. This configuration is useful for processing salts of weak acids, particularly organic acids derived from fermentation and related processes. The feed stream supplied to the salt/acid (S/A) loop 128 of the cell may, for example, be an ammonium or sodium salt of the organic acid at about pH of 4–7 and contain significant quantities (e.g. about 50 ppm each) of calcium and magnesium.

Under a direct current driving force, the salt is acidified in the S/A loop 128, while the ammonium or sodium ions are transported to the base loop 130. The cation membrane 132 may retain a substantial portion of the multivalent cations in the feed loop 126. However, depending on the acid being processed, the cation membrane 132 that is used, and the extent of the conversion of the feed stream to the product acid, a significant amount of the multivalent cations may get transported across membrane 132.

In the absence of the ion exchange column, the transported multivalent cations will precipitate in the high pH environment of the base loop 130, thereby preventing a reliable operation of the electrodialysis process. However, with the ion exchange column 114 in place, the multivalent cations are selectively and substantially removed from the base loop 130, thereby dramatically improving the apparatus and process operation. Since the ion exchange column 114 can maintain very low levels of the divalent metals in solution, the base loop 130 may be at any neutral or alkaline pH, i.e. pH 7–14.

The one constraint is that some cation membranes 132, such as the AQ cation membranes, and the Nafion® cation membrane (DuPont) exhibit significant levels of calcium transport, and are somewhat easily fouled at a high pH of about 14 by the transported calcium. For this reason, one preferred pH range for the base product has been found to be a pH in the range of about 7 to 13.5. For weak bases such as ammonia, this limitation occurs naturally. However, when dealing with sodium and potassium salts, mixtures thereof or mixtures of these salts with ammonium salts, a suitable neutralizing compound such as $SO_2$, $CO_2$, $NaHCO_3$ and the like may be added to obtain a base product within the target pH range. An addition of a liquid comprising water may be required in the base loop 130 in order to maintain the product base concentration at certain target levels. Once again the pH in the base loop should be maintained in the >7 range in order to ensure reliable operation of the ion exchange column 114 for removing the multivalent cations.

FIG. 5(c) shows a third version of the inventive apparatus. Here a three compartment cell 136 is used, with the ion exchange column 114 once again in communication with the base loop 138. This is the most versatile apparatus in the series of FIGS. 5(a)–5(c), since one can process the salts of either strong or weak acids, while yielding relatively pure acid and base products. Once again, in order to obtain reliable operation of the ion exchange column 114, the pH in the base loop is maintained at pH 7 or higher. As with the two compartment cation cell 126 (FIG. 5(b)), the cation membrane 140 may retain a significant portion of the multivalent impurities in the original feed salt, thereby reducing the load on the ion exchange column 114 in the base loop 138.

Many of the commercially useful products such as ammonia, sodium carbonate, potassium carbonate and sodium sulfite have a pH in the range of 9–11. Therefore, this pH range for the base loop is a preferred range for this apparatus. Weak acid ion exchangers have the best performance in terms of selectivity, capacity, stability and cost in this pH range and, therefore, are also preferred.

If the feed salt solution has relatively lower levels of calcium and magnesium, the use of the ion exchange column in the base loop is not required if the electrodialysis were to use cation membranes that are particularly selective to monovalent cations and sufficient dilution water containing stream added to the base loop in order to maintain the calcium, and magnesium concentrations below their solubility level in the base product.

Figure 6:
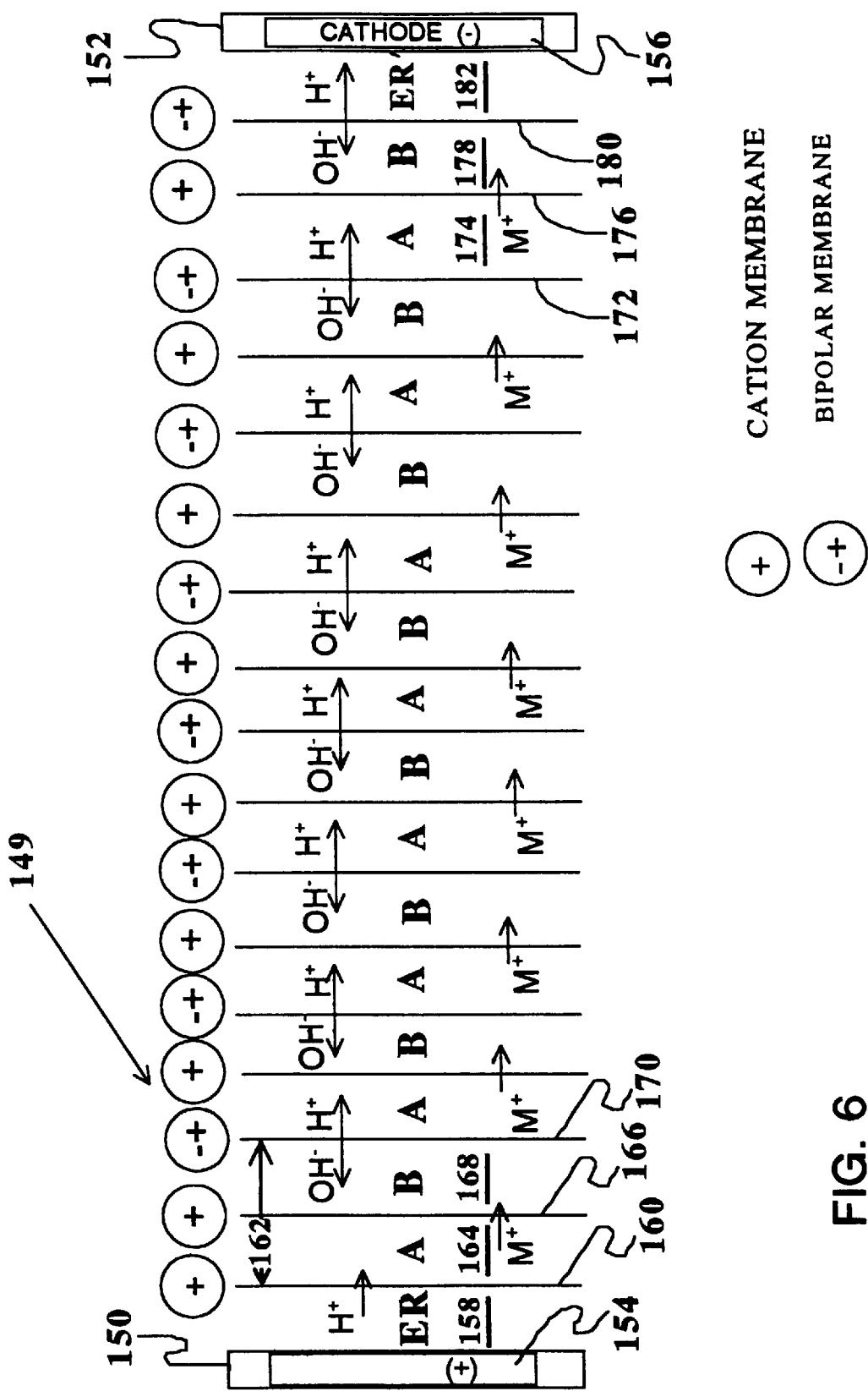
FIG. 6 is a schematic diagram showing the construction of the two-compartment cell used to demonstrate the utility of this invention.

The inventive apparatus and process are better understood from the following examples. All experiments were carried out using an eight cell, pilot, electrodialysis stack 149 that was assembled as shown in FIG. 6. All of the experiments were conducted in the two compartment cation cell using salts of weak acids to demonstrate the apparatus and process.

The stack 149 included end plates 150 and 152 to which the electrodes 154, 156 are attached and through which solutions were fed into and removed from the stack. Gaskets used to separate the membranes and form the solution compartments A and B were 0.76 mm thick. Each gasket had an open central area of 465 $cm^2$ (0.5 $ft^2$), through which current could pass. The open central areas are filled with an open meshed screen to keep the membranes separated as well as supported, and to promote good flow turbulence. Holes punched in the gaskets are aligned to form internal manifolds. Slots (ports) connecting the manifold with the open central area provide a flow of the solution into and out of each compartment.

The stack employed a coated metal (ruthenium) oxide anode 154, supplied by Electrode Products Inc.; an electrode rinse compartment (ER) 158, Sybron Chemicals MC 3475 cation membrane 160 (used because of its added strength) and seven repeating cells. Each cell (for example 162) includes acid compartment A 164, and a CMV, AQ, CMS, or CMT cation membrane 166. The AQ membrane is available from Aqualytics, a division of Graver Water, CMS membrane from Tokuyama Soda, while other membranes are products of the Asahi Glass Company. Each cell also includes base compartment B 168 and bipolar membrane 170, available from Aqualytics.

The last 172 of seven bipolar membrane in the stack 149 was followed by an acid compartment A 174, a cation membrane (the same type as in cells 1–7) 176, a base compartment B 178, another bipolar membrane 180, an electrode rinse compartment (ER') 182 and a stainless steel cathode 156.

Figure 7:
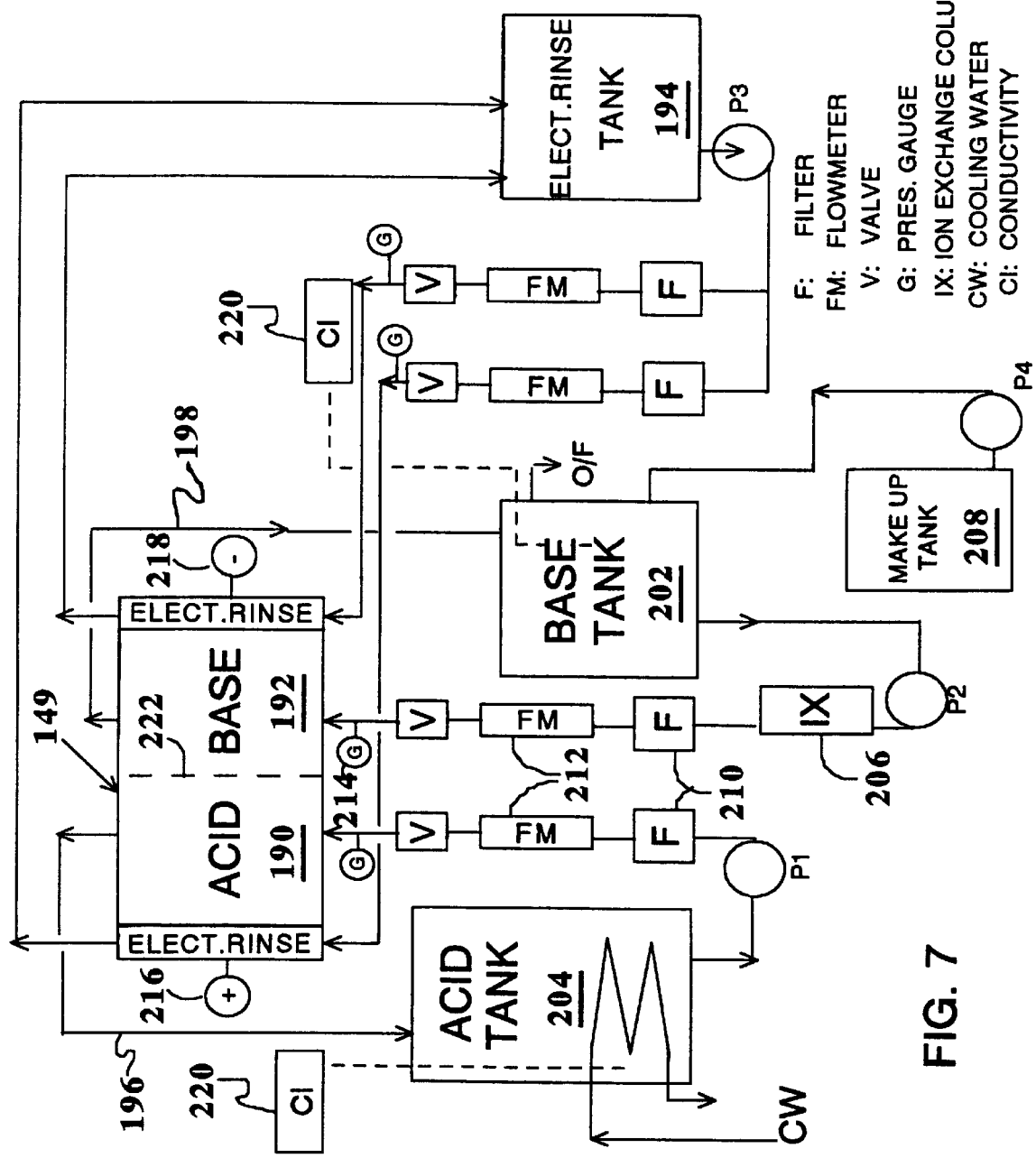
FIG. 7 is a block diagram showing a pilot system used for testing an apparatus of this invention.

The assembled stack 149 was placed in the system shown schematically in FIG. 7 in order to carry out the electrodialysis experiments. Three pumps (P1–P3) were used to circulate solutions to the acid (190), base (192) and electrode rinse compartments from their respective recycle tanks 204, 202, 194 at a rate of 2–3.5 1/min. The acid loop 196 was operated in a batch mode, while the base loop 198 was run in a feed and bleed mode. During operation, either fresh water or a salt solution may be added via a pump P4 from a make up tank 208, as needed. The base and the electrode rinse tanks 202, 194 each had a nominal volume of 5 liters, while the acid recycle tank 204 had the capacity to process as much as 180 liters per batch. A cooling water coil in the acid tank controls the temperature.

In some experiments, an ion-exchange column 206 containing a weak acid resin, IRC 84 from the Rohm & Haas Company, was used in the base recycle loop 198. Cartridge filters 210, flow meters 212 and pressure gauges 214 were used in each loop to ensure a flow of clear fluids at known flow rates and pressure drops in the three loops. A separate pump (not shown) was used to supply the feed salt solution to the acid recycle tank 204. A DC power supply (not shown) was hooked up to the anode and cathode terminals 216, 218 of the stack. The requisite controllers for providing and controlling the electrical current input and voltage are located in the power supply itself. Conductivity meters 220 were used in the acid and base loops to monitor the progress of the electrodialysis operation.

The system was initially charged with the requisite quantity of the filtered salt solution which was fed into the acid tank 204. A dilute alkaline solution along with a small amount of salt solution was added to the base tank 202 to provide the requisite electrical conductivity. The electrode rinse tank 194 was filled with about 5 wt % sulfuric acid. Recirculating pumps P1–P3 were started and the flows were adjusted in order to get an inlet pressure drop of 4–9 psi in each of the loops. The DC current was turned on and the amperage adjusted to obtain about 40A (80 A/ft² current density) at the start of the batch.

As the batch progressed, the conductivity of the acid solution decreased due to the transport of the monovalent cation ($NH_4^+$, $K^+$ or $Na^+$) across the cation membranes 222, and the concurrent formation of the acid in the acid loop. Consequently, the cell voltage increased as the batch progressed, until a set voltage limit of about 38V is reached (representing a unit cell voltage of about 4V, allowing 6 volts for the electrode rinse loops). The process continued with a decreasing current throughput.

The process is deemed complete when a target acid conductivity, typically 10 mS/cm, is reached. In the base compartment(s) 192, the monovalent cation combines with the $OH^-$ ions to form the base product. The electrical conductivity in the base loop was maintained at >10 mS/cm for most experiments through an addition of a salt solution, if needed. The addition of $CO_2$ was also made to the base loop when processing sodium lactate in order to maintain the pH in the loop at <13.5.

EXAMPLES

Three different salt feeds were processed to demonstrate the usefulness of this invention. The salts, ammonium lactate, sodium lactate and ammonium 2-keto levo gulonate ($NH_4$–2KLG) were products from the fermentation of dextrose. The pH of the salt solution ranged from 4.5 to 9, the electrical conductivity of 30–60 mS/cm, and a salt content of 70 to about 200 gm/l. All of the experiments were carried out at or near ambient temperatures (20–32° C.)

Example 1

The pilot cell was assembled with AQ bipolar membranes and CMV cation membranes. One hundred and six liters of ultrafiltered ammonium lactate solution was charged into the acid recycle tank 204. The conversion to acid was monitored through conductivity and pH measurements. The base loop 198 did not have an ion exchange column 206. The base tank 202 was initially charged with dilute ammonium hydroxide solution and as the ED process operated, the product ammonia solution overflowed from the base recycle tank 202. Small amounts of dilute NaCl solution were added to the base loop 198 to improve its conductivity. The process was deemed complete when the acid loop conductivity fell to around about 7 mS/cm.

The trial lasted approximately 15 hours. Samples of acid and base were collected and analyzed for lactic, ammonia and divalent metals. The results were as follows:

TABLE 1

| Run Time, min | Voltage V | Current A | Conducitivity, mS/cm Acid | Conducitivity, mS/cm Base | pH of Acid | Acid Volume, L | Acid Comp., gm/l Lactic | Acid Comp., gm/l $NH_3$ | Base Comp., gm/l $NH_3$ | Base Comp., gm/l Lactic |
|---|---|---|---|---|---|---|---|---|---|---|
| 0 | 0 | 0 | 42.37 | 23.3 | 5.8 | 106 | 80.4 | 15.3 | 43.71 | 14.6 |
| 2 | 33.5 | 40 | 42.45 | 23.5 | 5.42 | | | | | |
| 20 | 32 | 40 | 41.74 | 24.2 | 4.66 | 105.6 | 80.8 | 13.36 | 49.79 | 14.2 |
| 65 | 31.8 | 40 | 39.3 | 23.2 | 4.54 | 104.6 | 81.4 | 12.87 | 61.2 | 13.4 |
| 131 | 32.3 | 40.1 | 36.2 | 21.3 | 4.36 | | 81.7 | 11.9 | 65.33 | 12.2 |
| 190 | 32.9 | 40.1 | 33.46 | 19.9 | 4.18 | | 81.5 | 11.29 | 73.1 | 11.5 |
| 245 | 33.6 | 40.1 | 30.87 | 18.7 | 4.06 | | 80.8 | 9.71 | 59.26 | 11 |
| 349 | 35 | 40.1 | 26.51 | 16.7 | | 101 | | | | |
| 355 | 35.1 | 40.1 | 26.3 | 16.5 | 3.84 | | 83.6 | 8.5 | 81.6 | 10.5 |
| 480 | 37.2 | 40.1 | 21.1 | 15.1 | 3.63 | 99 | 83.4 | 6.44 | 84.51 | 10.2 |
| 488 | 38 | 36.2 | 21.47 | 15.8 | 3.55 | | 84.1 | 6.44 | 70.67 | 10.8 |
| 613 | 38.1 | 36 | 14.66 | 13.9 | 3.24 | | 85.2 | 3.89 | 76.5 | 10.6 |
| 778 | 38.1 | 31.3 | 9.14 | 13.3 | 2.96 | 96.2 | 87.3 | 2.55 | 76.74 | 11.7 |
| 889 | 38.1 | 28.7 | 7.27 | 13.2 | 2.86 | 96 | 87 | 2.18 | 72.86 | 12.5 |

The trial produced 96 liters of product at a lactic concentration of 87 gm/l. Ammonia removal was about 87%. As can be seen, the pH in the acid loop 196 decreases as the lactate salt is converted to the acid form. The average current input to the process was calculated at 36.4A (72.8A/ft$^2$). Lactic loss to the base loop 198 was calculated at about 1.5%. Overall current efficiency (i.e., equivalents of ammonia transported per faraday of current input) was approximately 55%.

The following Table summarizes the transport of the metals from the acid to the base loop 198 across the CMV cation membranes. During the test, the Na, Ca and Mg levels in the acid decreased, while these levels increased in the base. Also shown is the percent retention of these ions in the base loop 198 as a function of residual ammonia concentration in the acid loop. The retention figures are shown cumulative, i.e., from the start of the process.

TABLE 2

| Run Time, min. | NH$_3$ in acid, gm/l | % Conv. | Acid analysis, ppm Na | Ca | Mg | Fe | Base analysis, ppm Ca | Mg | Fe | % Retention in acid loop Na | Ca | Mg |
|---|---|---|---|---|---|---|---|---|---|---|---|---|
| 0 | 15.3 | 0 | 164 | 17.2 | 24.8 | 0.58 | 16.1 | 36 | N.D. | 100 | 100 | 100 |
| 2 | | | | | | | | | | | | |
| 20 | 13.36 | 13 | 110 | 16.5 | 24.3 | 0.58 | 18 | 22.7 | N.D. | | 95.6 | 97.6 |
| 65 | 12.87 | 17 | 136 | 16.2 | 24 | 0.6 | 17.8 | 12.1 | N.D. | | 93.0 | 95.5 |
| 131 | 11.9 | 24 | 167 | 15.6 | 23.9 | 0.58 | 14.5 | 9.73 | N.D. | | 89 | 94.6 |
| 190 | 11.29 | 28 | 185 | 15.2 | 238 | 0.57 | 13.6 | 9.84 | N.D. | | 86.1 | 92.8 |
| 245 | 9.71 | 39 | 197 | 14.6 | 23.5 | 0.56 | 13.8 | 9.85 | N.D. | ~100 | 81.7 | 91.2 |
| 349 | | | | | | | | | | | | |
| 355 | 8.5 | 48 | 206 | 13.4 | 22.7 | 0.62 | 13.1 | 8.79 | N.D. | | 73.5 | 86.4 |
| 480 | 6.44 | 61 | 200 | 12 | 22.1 | 0.61 | 11.3 | 5.69 | N.D. | | 65.5 | 83.6 |
| 488 | 6.44 | 61 | 189 | 12 | 22.7 | 0.64 | 11.3 | | N.D. | | 64.5 | 84.4 |
| 613 | 3.89 | 77 | 162 | 11.1 | 22.4 | 0.68 | 6.8 | 5.65 | N.D. | 94 | 59.7 | 83.1 |
| 778 | 2.55 | 85 | 138 | 10.7 | 22.8 | 0.73 | 7.7 | 3.72 | N.D. | 76 | 56.5 | 83.4 |
| 889 | 2.18 | 87 | 120 | 10.5 | 22.7 | 0.79 | 7.8 | 3.57 | N.D. | 66 | 55.2 | 82.9 |

The pH in the base loop 224 was about 10–10.5. The solubility of the divalent metals in the base loop 198 is estimated at 8–20 ppm for calcium and 4–10 ppm for magnesium. As the batch progressed, the decreasing levels of Ca and Mg in the base loop indicates a tendency for the precipitation of these metals in the base loop with time. It can be seen that the CMV cation membranes retain significant amounts of the multivalent metals, particularly magnesium and iron. In specific terms about 100% of the iron, about 83% of the magnesium, and about 55% of the calcium are retained in the acid loop.

At the conclusion of the experiment, the CMV membranes were visibly in excellent physical condition and were not fouled by the divalent cations.

Example 2

The Example 1 was repeated after replacing the CMV cation membranes with AQ cation membranes. A hundred six and one half liters of the ammonium lactate feed were processed over 817 minutes to yield a product acid containing 1.58 gm/l NH$_3$ at an average current input of 33.2 A (66.4 A/ft$^2$). Ammonia removal was about 92%. The lactic loss via diffusion to the ammonia loop was about 2.8%. The overall current efficiency for the process was about 68%. However, metals analysis showed that the retention of the divalent metals was lower than for CMV; about 42% for magnesium, and about 37% for calcium. Therefore, the ammonia solution from the test had higher levels of dissolved metals: about 10–19 ppm calcium and 5–31 ppm magnesium. At the end of the experiment, the AQ cations were somewhat mottled in appearance, indicating possible fouling by the divalent cations.

Example 3

Eight batches of ammonium lactate feed containing 70–92 gm/l lactate, with an initial conductivity of 28 to 42 mS/cm, were processed in the pilot cell. The cell contained AQ bipolar membranes, and CMV cation membranes that were used in Example 1. The input feed streams were subjected to ultrafiltration (200,000 Daltons cutoff). There was no ion exchange column 206 in the base loop 198. Ammonium hydroxide was at a concentration of 30–66 g/l and conductivity of 11 to 32 mS/cm was generated in the base loop 198. A diffusion of a small amount of lactic anion into base loop 198 provided the requisite conductivity in the loop. No water or salt solution addition was made during these operations.

The batches were of varying size and lasted from 6.35 to 40.3 hours. Each batch was terminated when the acid loop conductivity had decreased to about 7–10 mS/cm. During the batches, the ammonium ion concentration in the acid loop 196 dropped from 7–12 gm/l to 1.1–3.6 gm/l.

The total cell voltage was limited at about 38 Volts for each batch. The current input, which was limited at 40 A (representing an initial current density of 80 A/ft$^2$) decreases as the batch progressed. For each batch the average current input was calculated. The results were as follows:

TABLE 3

| | Metals in the feed, ppm | | | Average Values | |
|---|---|---|---|---|---|
| Batch No. | Ca | Mg | Batch Duration, Hours | Current A | Voltage V |
| 1 | 17.6 | 36 | 6.35 | 37 | 37 |
| 2 | 20 | 45 | 8 | 37 | 37 |
| 3 | 43 | 23 | 23.5 | 34 | 38 |
| 4 | 25 | 45 | 13.3 | 31.4 | 37 |
| 5 | 20 | 46 | 18.75 | 30 | 38 |
| 6 | 24 | 46 | 40.3 | 26 | 38 |
| 7 | ~20 | 56 | 15 | 23 | 38 |
| 8 | 18 | 56 | 15.3 | 20.5 | 38 |

The cell was opened and inspected at the conclusion of the operations. The bipolar membranes and CMV cation membranes were in good condition, with no physical evidence of fouling. However, there was a certain amount of precipitates in the base compartments 192, which was easily washed off. The precipitate was analyzed and found be 16.4% Ca, 2.5% Mg, 0.5% Na, 0.1% K and 350 ppm Fe. These operations demonstrate the progressive decrease in the current throughput, arising from presence of the divalent metals in the feed stream and their transport to the alkaline environment in the base compartments 192. A plugging of the base compartments 192 and a blockage of the bipolar membrane surface by the divalent cations had decreased the cell performance.

Example 4

Four batch experiments were carried out using a sodium lactate feed stream derived via fermentation. The ultrafiltered feed solution which had a pH of about 5.4, contained about 105 gm/l of lactic in the form of its sodium salt as well as about 21 ppm Ca, and 62 ppm Mg. The feed salt had a sodium content of ~25 gm/l. The pilot cell contained eight AQ bipolar membranes, seven CMV cation membranes (one new and six of them from earlier Examples 1, 3,) and one new AQ cation membrane. The cell voltage was once again limited at 38 Volts. Water was added to the base loop 198 at the rate of 10 ml/min in order to keep the product alkali concentration below about 2.5N. There was no ion exchange column 206 in the base loop 198. Carbon dioxide was bubbled into the base loop in order to maintain the pH therein below about 13.5. During the electrodialysis process, the feed conductivity decreased from about 34 mS/cm to about 9.5 mS/cm, with the residual sodium content in the acid being 3.5–4.0 gm/l. Details on the cell performance follow:

TABLE 4

| Batch No. | Dura-tion min. | Average values Voltage V | Average values Current A | Acid batch volume L | Conver-sion of lactate to acid % | % Metals retained in acid Ca | % Metals retained in acid Mg |
|---|---|---|---|---|---|---|---|
| 1 | 290 | 38 | 26 | 28→25.2 | 85 | 86 | 94.7 |
| 2 | 1218 | 38 | 26 | 109→98 | 85 | 81 | 98 |
| 3 | 1400 | 38 | 26 | 132→118 | 82 | 90 | 93 |
| 4 | 1478 | 38 | 25.3 | 132→118 | 82 | >99 | 98 |

The retention of the divalent metals by the cation membranes in these operations was superior to that observed with ammonium lactate in Example 1. This is probably due to the relatively higher concentration of the of the monovalent cation (sodium in this instance) and higher current efficiency for sodium vs. Ammonium (the absence of back diffusion losses), the use of dilution water to keep the transported divalent ions in solution as well as the lower conversion of the lactate salt.

The cell was opened and inspected. The bipolars and CMV cation membranes were in excellent condition without any physical evidence of fouling. The AQ cation membrane was cloudy/opaque and appeared to be fouled. The internal parts of the cell were clean, because the high retention of the divalent cations by the (CMV) cation membranes resulted in low levels of divalent metals in the base loop 224 (<5 ppm Mg and <20 ppm Ca). The precipitation problems will undoubtedly occur with higher levels of the divalent metals in the feed stream, lower feed concentration, or higher process conversions.

Example 5

A test on the conversion of ammonium-2 keto gulonic acid ($NH_4$–2KLG) to the free acid 2 keto gulonic acid (2KLG) was carried out in the pilot cell containing AQ bipolar and AQ cation membranes. The starting solution was obtained by neutralizing a fermentation derived sample of 2KLG with ammonia, containing 170 gm/l 2KLG and 12.99 gm/l $NH_3$ equivalents, and having a pH of about 9. Twenty eight liters of the feed was processed in the electrodialysis cell, with the conductivity decreasing from 35.1mS/cm to 8.6 mS/cm due to acidification and the concurrent transport of ammonia out of the feed loop extending to feed tank 200. The NaCl solution was added to the base loop 198 during the process in order to maintain a conductivity therein of 16–20 mS/cm. Once again, there was no ion exchange column 206 in the base loop 198. The results were as follows:

TABLE 5

| Run time min | Voltage V | Current A | Acid Conductivity mS/cm | Acid loop analysis 2KLG gm/l | Acid loop analysis pH | Acid loop analysis $NH_3$ gm/l | Acid loop analysis Ca ppm | Acid loop analysis Mg ppm | acid volume L | Base loop analysis, ppm Ca | Base loop analysis, ppm Mg |
|---|---|---|---|---|---|---|---|---|---|---|---|
| 0 | 0 | 0 | 35.1 | 170 | 9.1 | 12.99 | 21.9 | 5.62 | 28 | 24.3 | 0.18 |
| 6 | 38 | 34 | 35.4 | | | | | | | | |
| 11 | 35.1 | 40 | 38.2 | 175 | 8.6 | 11.17 | 20.3 | 4.86 | | 27 | 0.59 |
| 21 | 32.7 | 40 | 35.1 | | | | | | | | |
| 27 | 32.3 | 40 | 38 | 174 | 4.74 | 10.61 | 19 | 4.52 | ~28 | 29.1 | 1.18 |
| 33 | 32.3 | 40 | 34.4 | | | | | | | | |
| 85 | 34.1 | 40 | 28 | 178 | 3.32 | 6.0 | 16.3 | 3.44 | 27.5 | 40.1 | 6.43 |
| 118 | 36.6 | 40 | 23.1 | 180 | | 4.33 | 13.2 | 2.67 | | 51.8 | 9.75 |
| 125 | 34.2 | 40 | 22.2 | | | | | | | | |
| 143 | 34.9 | 40 | 19.2 | 181 | 2.73 | 3.35 | 10.4 | 2.04 | 26.5 | 57.1 | 11.5 |
| 211 | 38.1 | 40 | 11.5 | 186 | 2.12 | 1.40 | 3.36 | 0.63 | ~26 | 79 | 15.8 |
| 255 | 38.1 | 38.2 | 9.5 | 189 | 2.01 | 0.84 | 1.28 | 0.23 | 25.5 | 87.6 | 17 |
| 283 | 38.1 | 37.9 | 8.6 | 190 | | 0.73 | 0.59 | 0.13 | | 91.7 | 17.7 |

The final product contained 190 gm/l 2KLG and only 730 ppm $NH_3$, representing about 95% removal of the cation from the salt. The current efficiency was about 40%. It can be seen that substantially all of the calcium and magnesium values in the feed salt have been transported across the AQ cation membranes. This is in dramatic contrast with the results obtained with the sodium lactate test in Example 4. At least in part, the high level of divalent cation transport is likely due to the lower retention by the AQ cation membranes (see Example 2), but may also occur either because 2KLG is an acid which is a much stronger acid than lactic or 2KLG was not able to bind very well with the divalent cations. This large transport substantially increased the concentrations of the metals in the base loop 202. The metals, about 20 ppm for Mg and about 100 ppm for Ca, remained in solution, since the pH in the base loop 224 was only in the range of 10–11.

Solubility Data for Divalent Ions as a Function of pH

Thirty seven batches of ammonium and sodium lactate and $NH_4$–2KLG feeds were processed in the pilot assembly, with the processing of each batch lasting from 6 to >24 hours. The lactate feeds were from the fermentation of dextrose. The 2KLG feed was obtained by neutralizing the acid with ammonia. Each of the feeds were subjected to simple filtration or to ultrafiltration prior to processing in the electrodialysis cell. The feeds had 20–150 ppm Ca and 6–60 ppm Mg. When processing the sodium lactate salt, the pH of the sodium alkali base product was limited by the addition of gaseous $CO_2$.

Samples of the product base were analyzed for both their divalent metal content and their pH. There was no ion exchange column 206 in the base loop 198, so that the measured concentrations of these ions represent their solubility in the base loop. The CMV or CMT cation membranes were used in these processings. The CMV membrane was used in the first eighteen and the CMT membrane in the later nineteen tests. Both cation membrane remained in excellent condition after the processings, with no visible evidence of fouling by multivalent cations in the feed.

Figure 8:
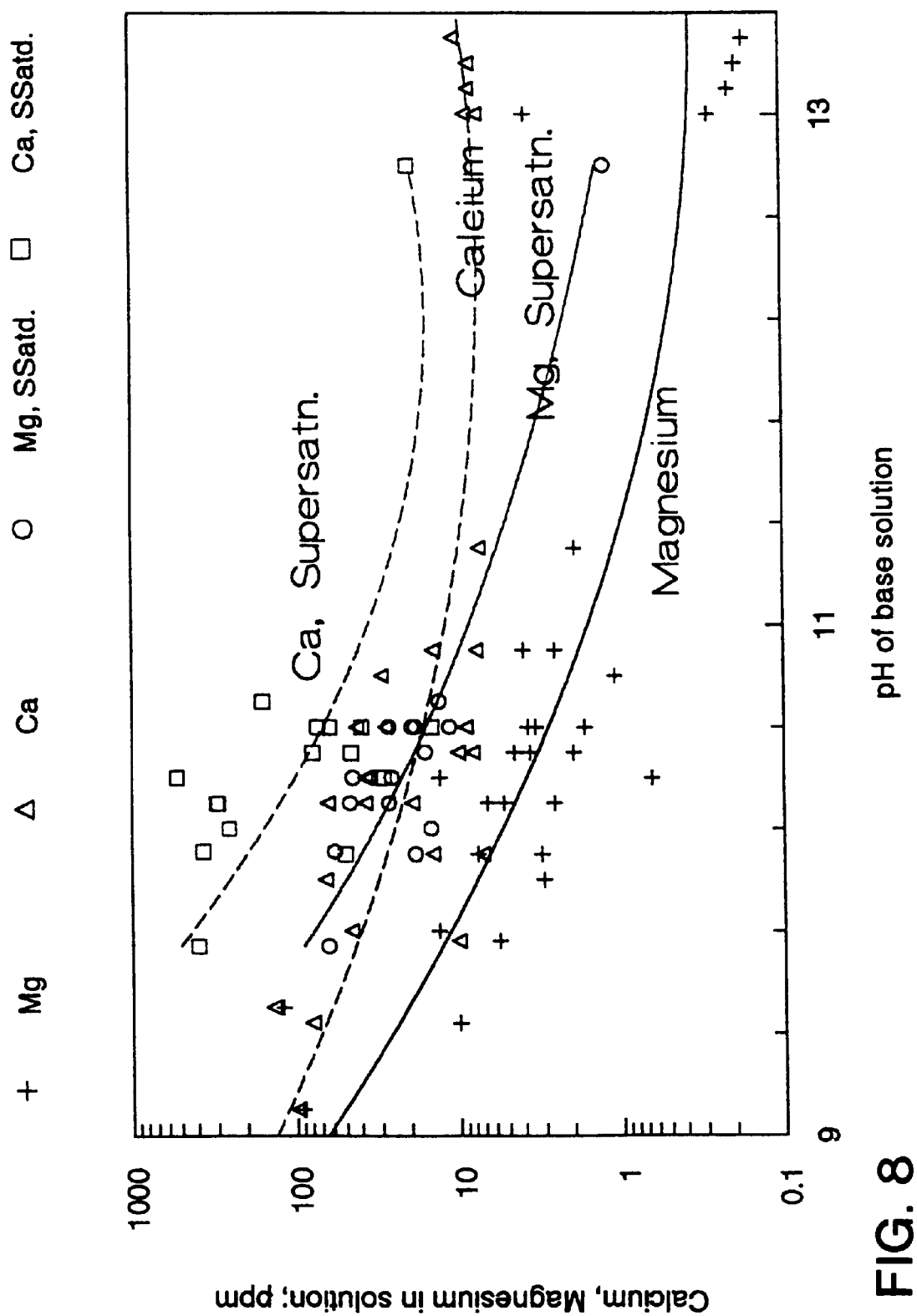
FIG. 8 is a graph summarizing the solubility data of calcium and magnesium, as a function of base pH.

The results of the study on solubility as a function of pH are plotted in FIG. 8. When producing ammoniacal base solutions the pH ranged from 9 to about 11.4, while the sodium alkali solutions had a pH range of about 12 to 13.4.

cleaning was obtained by washing the loop with a dilute solution of a strong acid, preferably HCl. However, such a step involves unscheduled downtime and reduced process throughput with the potential for mechanical damage to cell hardware due to heating, meltdown etc. There is also a potential long term damage to the bipolar membranes as a result of heavy surface precipitation, blistering, etc.

The inventive apparatuses and processes enable a long term trouble free operation of the electrodialysis cell by maintaining the divalent metal concentrations in the base loop, either below or near their solubility limits. In one preferred pH range 9.5–11 of this invention, the target levels are about 2–25 ppm for Mg and about 20–100 ppm for Ca. For a prolonged trouble-free operation of the ED cell, one needs to maintain the divalent metal at a somewhat lower level, say 2–10 ppm Mg and 10–25 ppm Ca, this being governed by the dynamics of the process, since the anion surface of the bipolar membrane which generates the $OH^-$ ions is at a pH of about 14. By maintaining an adequate fluid velocity within the base compartments, there is a sustained reliable long term operation at high current throughput.

It is important to note that the data shows a solubility of >10 ppm for calcium at a pH value of 14. If such low levels of calcium can be maintained in the base loop, the extended term production of dilute alkalis (0–15 wt %) such as sodium or potassium hydroxide can be achieved.

Example 6

Ammonium lactate made in a fermenter was filtered by using a nanofiltration unit. The filter Desal 5-DK made by Desalination Systems was used for this purpose. The product from this filtration step had about 90 gm/l of lactate, 10–13 gm/l ammonia as ammonium cation, 11 ppm calcium and 9 ppm magnesium. The feed, at a pH of about 5, was then processed in the pilot cell as described in Example 1. The pilot cell contained eight AQ bipolar membranes and six CMV cation membranes taken from Example 1 and two new AQ cation membranes. Six consecutive batches of about 120 liters of feed per batch were processed in a manner similar to Example 1. The results are summarized below:

TABLE 6

| Batch number | Duration, hr. | Average values | | Acid conc. gm/l | | Acid loop conductivity mS/cm | Ammonia in acid, gm/l | |
|---|---|---|---|---|---|---|---|---|
| | | Current A | Voltage V | Initial | Final | | Start | End |
| 1 | 28.1 | 21 | 39 | 91 | 94 | 35→8 | 10.44 | 2.7 |
| 2 | 24 | 25.7 | 38 | 76 | 90 | 38→8 | 13.9 | 2.2 |
| 3 | 25.5 | 26 | 38 | 82 | 87 | 39.6→8.3 | 15.4 | 2.1 |
| 4 | 23.7 | 28 | 38 | 92 | 98 | 39.1→5.6 | 13.9 | 1.14 |
| 5 | 24.7 | 28.5 | 38 | 93 | 98 | 39.1→7.4 | 11.7 | 2.0 |
| 6 | 24.5 | 28 | 38 | 79 | 90 | 40→6.7 | Not measured | |

The data could be divided into two sections for each of calcium and magnesium. One set of data represents the solubility limit, while the second set of data represents a supersaturated state where the alkaline solution can hold significantly higher levels of the divalent metals.

However, there is always the potential for spontaneous precipitation and the consequent plugging of the base loop of the electrodialysis cell. It should be pointed out that the base loop could be cleaned and the cell performance restored, as had been done on occasion in the laboratory. The It can be seen that the batches were quite reproducible in terms of current input, voltage drop and conversion of the salt to acid. At the conclusion of the study of six batches the cell was opened. The internal parts were clean and free of precipitates, demonstrating that the use of nanofiltration, coupled with the retention of the multivalent cations afforded by the cation membranes was effective in maintaining stable long term performance.

The use of nanofiltration results in a generation of a concentrate (termed retentate) stream that contains a portion of the feed salt as well the bulk of the divalent metals. The stream may be disposed of after suitable treatment. This disposal represents a lost resource. However, in many instances, such as in a fermentation operation, the stream may be returned back into the front end and recovered.

Example 7

A pilot system was setup in the mode shown in FIG. 7 with the ion exchange column 206 in place. The electrodialysis cell contained eight AQ bipolar membranes and eight CMT cation membranes. Both types of membranes were taken from the long term studies detailed earlier. The ion exchange column 206 in the base loop 198 was filled with IRC 84 resin (a weak acid cation exchange resin) from Rohm and Haas and converted to the ammonium form prior to the trials.

Feed ammonium lactate for the trials had been ultrafiltered in a unit rated at about 200,000 Daltons and contained typically 40–150 ppm Ca and 45–65 ppm Mg. Lactate content in the feed ranged from 60–100 gm/l.

Thirty batches of the feed ammonium lactate were processed in a manner analogous to the processing in Examples detailed before. Each of the batches lasted 6 to 24+ hours with each batch being terminated when the acid loop conductivity dropped below about 10 mS/cm. Detailed measurements showed the CMT and CMV membranes had similar levels of retention for multivalent cations.

The ion exchange column was effective in maintaining the divalent metal concentrations at low levels in the base loop. During the initial batch following a regeneration of the column the levels of calcium and magnesium in the base loop were in the order of 0–2 ppm each. The levels gradually increased during subsequent batches, principally because of the kinetic limitations of a relatively short column (<2 feet deep) and a high service flow rate. When the divalent metal concentration reached about 10 ppm total, after about four batches of 140–180 liters each, the column was regenerated and reused in the subsequent batches. In this manner a stable long term operation of the electrodialysis cell was achieved, with steady current throughputs and voltage drops.

The apparatus combining the electrodialysis cell with an ion exchange column in the base loop enabled the electrodialysis cell to operate over extended periods without the need for routine acid cleaning of the base loop. In fact, a certain amount of buffer capacity exists within the improved apparatus. The ion exchange column is able to clean the base loop simply by having the base solution circulating in the apparatus with the electrical power turned off.

For the inventive apparatuses and processes, cation membranes that have a high level of retention for the divalent cations are preferable because they reduce the level of these ions in the base loop. Therefore, they reduce the load on the ion exchange column. The higher retention membranes CMV and CMT have been found to be not prone to fouling by the divalent cations. It is believed that these membranes are prepared by using cross-linked polymerization of styrene and divinyl benzene onto a suitable substrate. These and similarly made cation membranes, which we will term the "monovalent favoring type" are the preferred ones for the inventive apparatuses of this invention. In this context, the "monovalent selective" type membrane (such as the CMS membrane from Tokuyama Soda) are the most preferable.

The apparatus of this invention can be used to improve many processes involving the production of acids and bases from salts. Three such applications are shown schematically in FIGS. 9 through 12.

Figure 9:
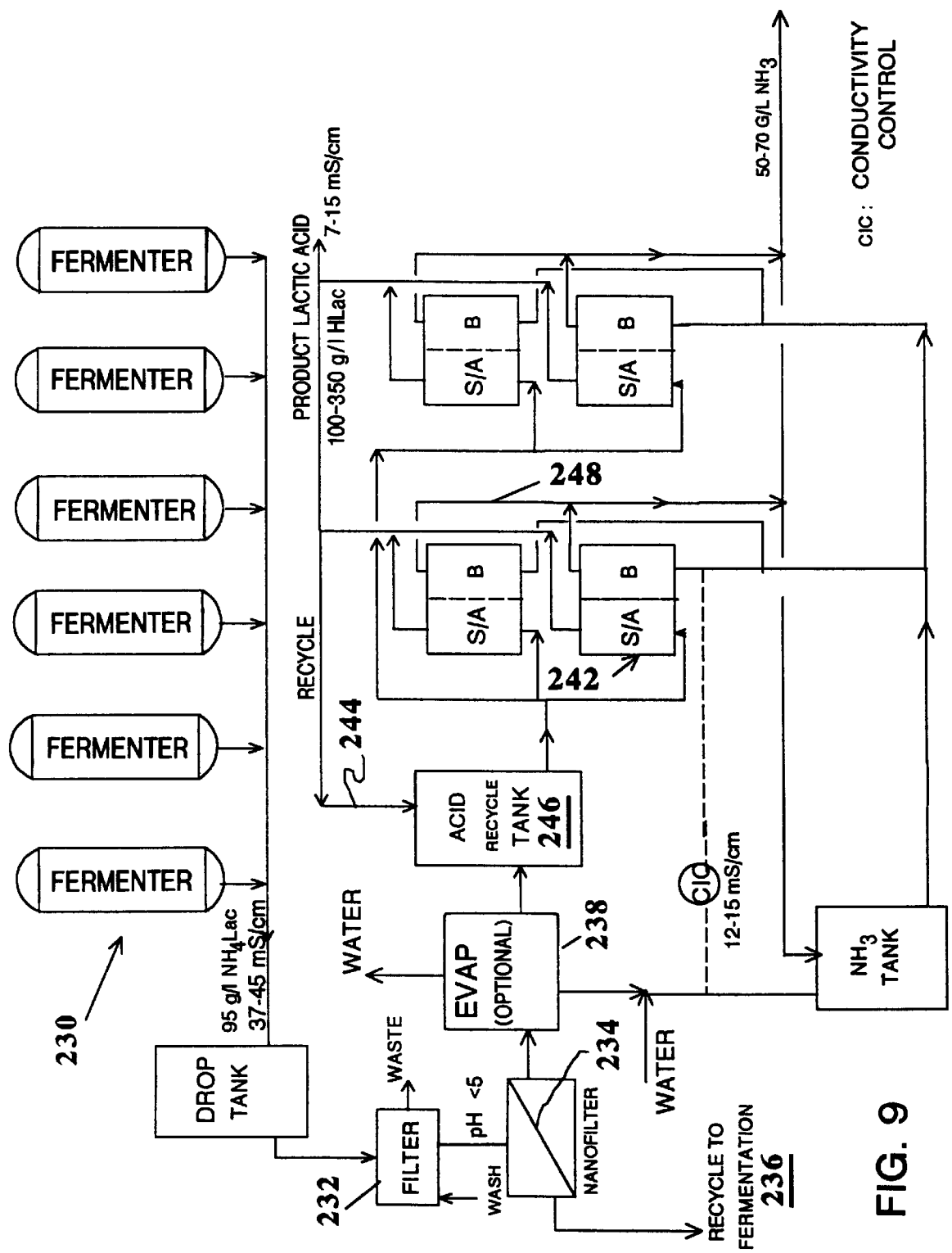
FIG. 9 is a block diagram which shows the use of this invention in the production of organic acid via fermentation.

FIG. 9 shows the use of one version of the inventive apparatus in the production of low molecular weight monovalent organic acids. A bank 230 of fermenters may be operated in a batch mode to produce the organic acid in its salt form. For optimum productivity the fermentation is conducted at a pH of about 4–7. The pH is maintained through an addition of an alkali. Ammonia is a preferred alkali because of its low cost and the ease of its recovery in a downstream electrodialysis operation.

The product organic salt is then filtered at 232 to remove any insoluble cell mass and subsequently nanofiltered at 234. The retentate from the nanofiltration unit is recycled at 236 to the fermenters. The nanofiltrate may be further concentrated via conventional evaporation at 238 if desired and fed to the acid recycle tank 246 of the electrodialysis cells.

One or more electrodialysis process units 242, each containing two hundred or more electrodialysis cells may be employed to obtain the requisite product throughput. The electrodialysis (ED) cells are of the two-compartment cation type, such as shown in FIGS. 1(b), 2(a) or 3. The acid loop 244 is operated in a batch mode, with the product acid being pumped out of the acid recycle tank 246 when the target conversion is realized. A fresh batch of feed is then added to the acid recycle tank and the process continued.

Ammonium hydroxide is generated in the base loop 248 of the ED cells. The base loop may be operated in a preferred steady state feed and bleed mode or in a batch mode. Dilution water and a small amount of a salt solution may be added to the base loop, if necessary, in order to maintain the product ammonia concentration and conductivity at certain target levels. The process is suitable for processing a number of organic acids such as acetic and lactic.

A three compartment cell such as shown in FIG. 1(c) or FIG. 2(b) may used in place of the two compartment cation cell for producing higher purity acids or processing salts of stronger acids.

Figure 10:
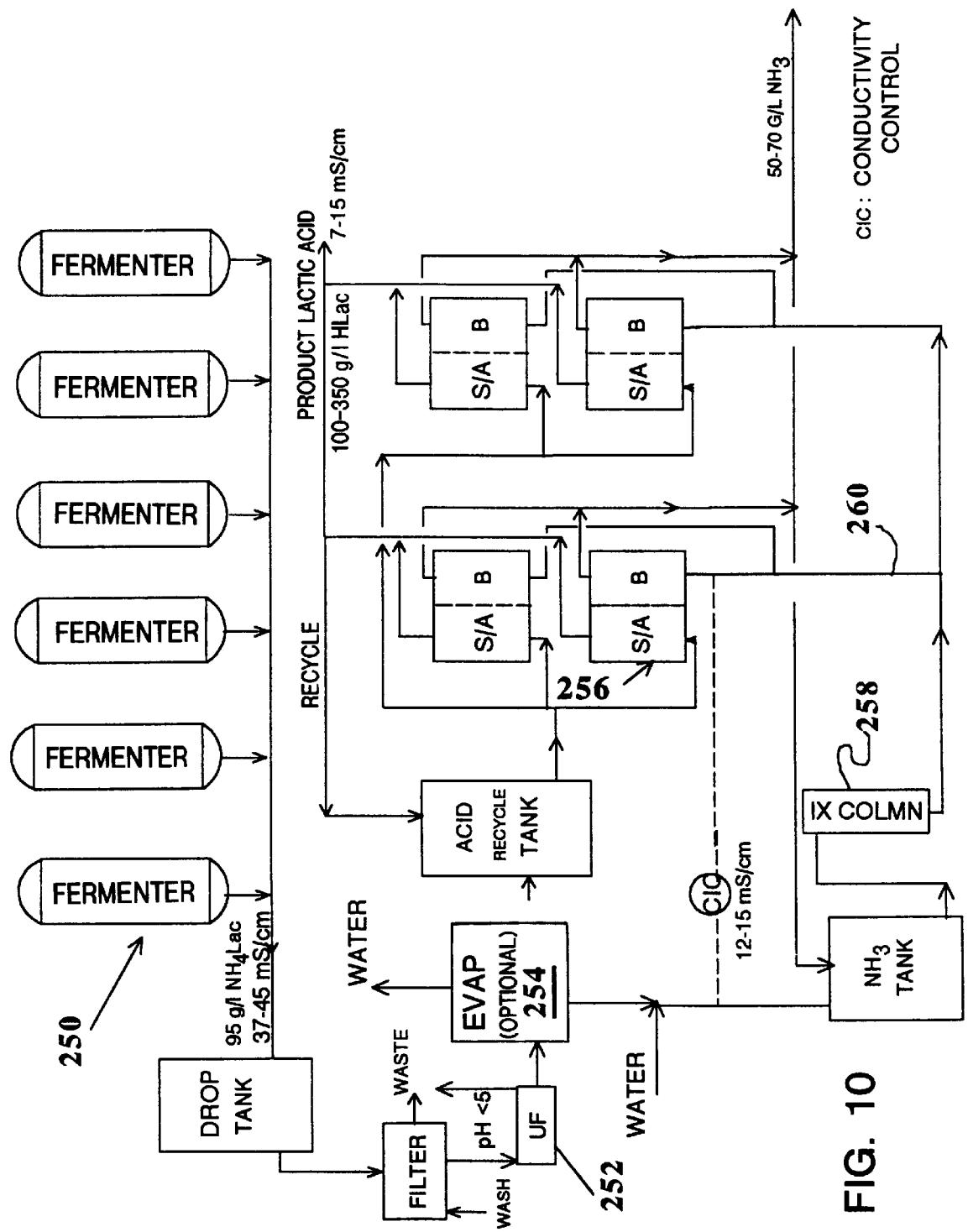
FIG. 10 and 10a are block diagrams which shows other aspects of this invention in the production of organic acid via fermentation.

FIG. 10 shows another version of the process employing another of the inventive apparatus. In this example, the product organic salt from the fermenters 250 is once again filtered to remove the cell mass and the insoluble impurities via a coarse ultrafilter 252 (typically 200,000 Daltons rating). The filtrate usually contains 70–110 gm/l of organic salt. The organic salt may optionally be concentrated further via conventional evaporation 254 prior to processing in the two compartment ED cell 256. The concentration step has the advantage that it stabilizes the feed organic salt against further microbial growth, as well as improving the product recovery and process efficiency of the ED recovery step.

The ED cell 256 has an ion exchange column 258 in communication with the base loop 260. During the processing operation, the ion exchange column, containing a weak acid cation exchange resin, keeps the multivalent cation levels in the base loop 260 at or below their solubility limits (occasional excursions above the solubility may be tolerated because of the built-in buffer of the ion exchange column).

Depending on the acid being produced and the product purity desired, any one of the cells shown in FIGS. 1–3 (or similar ones) may be used in place of the two compartment cell 256 that is shown. The apparatus incorporating the ion exchange column 258 in communication with the base loop 260 of the ED cells 256 is generic and versatile. The apparatus can process salts of either weak or strong, monovalent or multivalent acids. Examples of acid that can be processed by the apparatus include acetic, lactic, formic, citric, gluconic and 2KLG.

Figure 11A:
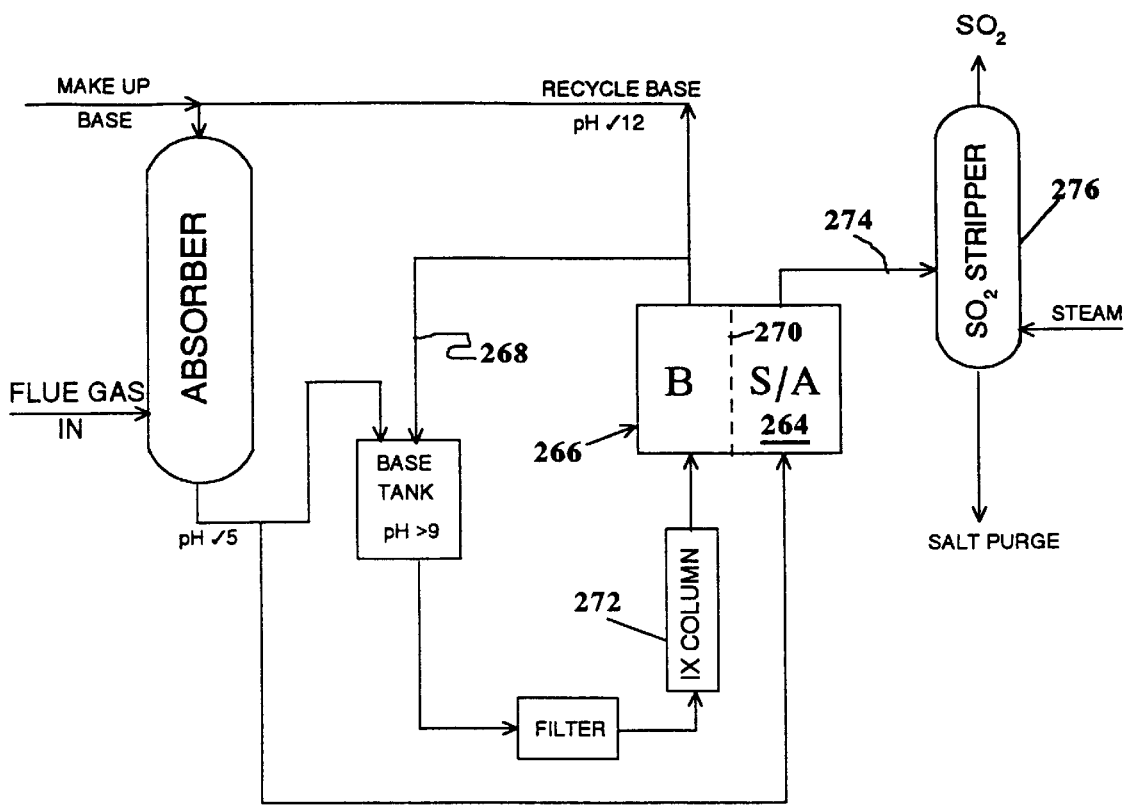
FIGS. 11(a)–11(b) are block diagrams showing flue gas desulfurization process systems using the apparatus of this invention.
Figure 11B:
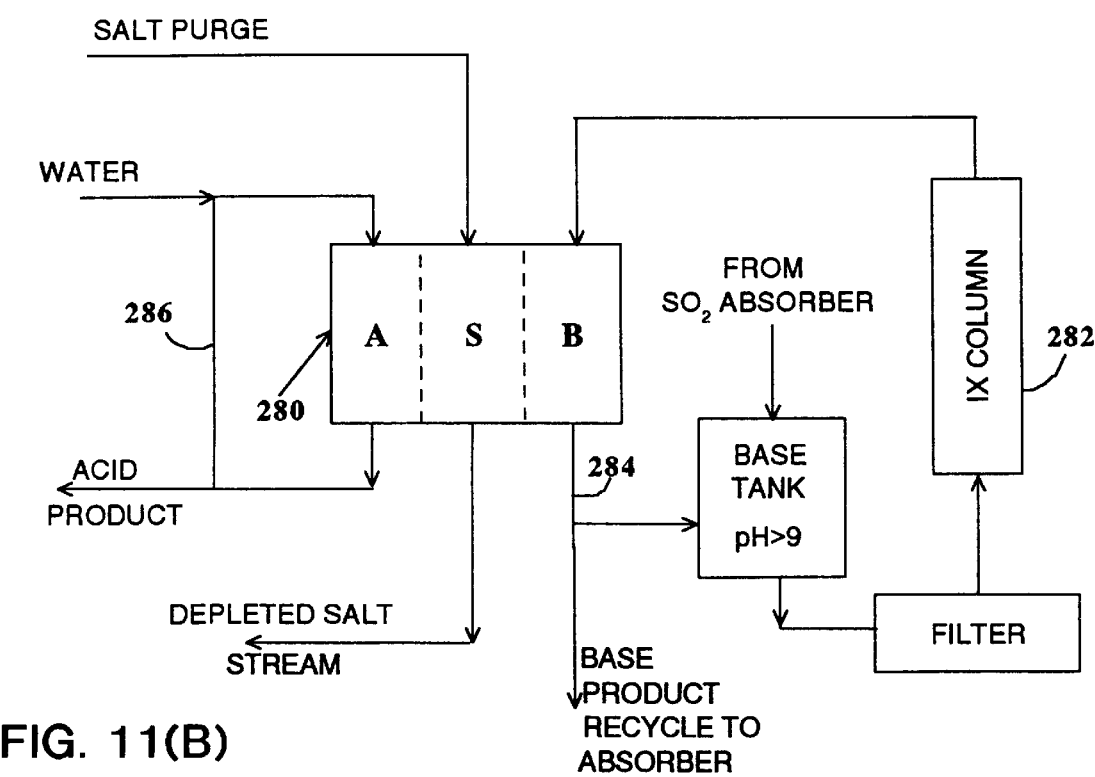

FIGS. 11(a)–11(b) show the applicability of the inventive apparatus in the recovery of sulfur dioxide from flue gases. The basic process is described in some of the patents cited earlier and marketed by the Allied Signal Corporation as the SOXAL® process. In the process, sulfur dioxide from the flue gases of power plants or other sources is absorbed in a solution of sodium sulfite and sodium hydroxide (pH 9–12) to yield a salt, sodium bisulfite. In the process a certain portion of the feed sulfite is oxidized to sulfate.

In the recovery process shown in FIG. 11(a), a portion of the bisulfite product, which may have some unconverted sulfite, usually at a pH of about 5–5.5, is fed to the acid compartment 264 of a two compartment cation cell (as for example FIG. 1(b)) 266 while the remainder of the bisulfite product is fed to the base loop 268. The bisulfite product also tends to have significant amounts of dissolved calcium, magnesium and other multivalent metal species derived from the flue gas source. These metals precipitate in the base loop 268 of the ED cell 266, thereby causing significant operational problems.

In the ED cell 266 of FIG. 11(a), in addition to the sodium ions, a portion of the divalent cations are transported across the cation membranes 270 to the base loop. The divalent cations, along with those cations added with the makeup bisulfite are removed from the base loop 268 by the ion exchange column 272. The use of the inventive apparatus and process shown in FIG. 11(a) eliminates or greatly mitigates this problem so that long term reliable operation of the process can be achieved. The divalent cations retained in the acid loop 274 are removed along with the sulfate after removing the $SO_2$ product in a stripper 276. Potassium or ammonium or mixtures of monovalent cations may be used in place of sodium if desired.

The sodium sulfate solution from the $SO_2$ stripper may be processed in a three compartment cell after a suitable pre-treatment to remove the multivalent metals in order to generate additional alkali and byproduct sulfuric acid. In a preferred mode the sulfate solution has a certain amount of free sulfuric acid to enable substantially a complete recovery of $SO_2$ in the stripper. As a result, the sulfate stream would be acidic in the pH range of 3–5.

FIG. 11(b) shows the use of an improved apparatus in recovering the acid, base values from the acidic sulfate stream. The sulfate stream is fed to a three compartment cell 280 incorporating an ion exchange column 282 in communication with the base loop 284. A portion of the sodium sulfate is converted to a byproduct sulfuric acid and a base which is suitable for recycling to the absorber. A portion of the unconverted sulfate values, along with the multivalent metals present in it, may be discharged as a purge from the salt loop, while the balance is recycled. As a further option, the base loops of the two and three compartment cells in FIGS. 11(a) and 11(b) may be set in communication with a common ion exchange column if desired.

Figure 12:
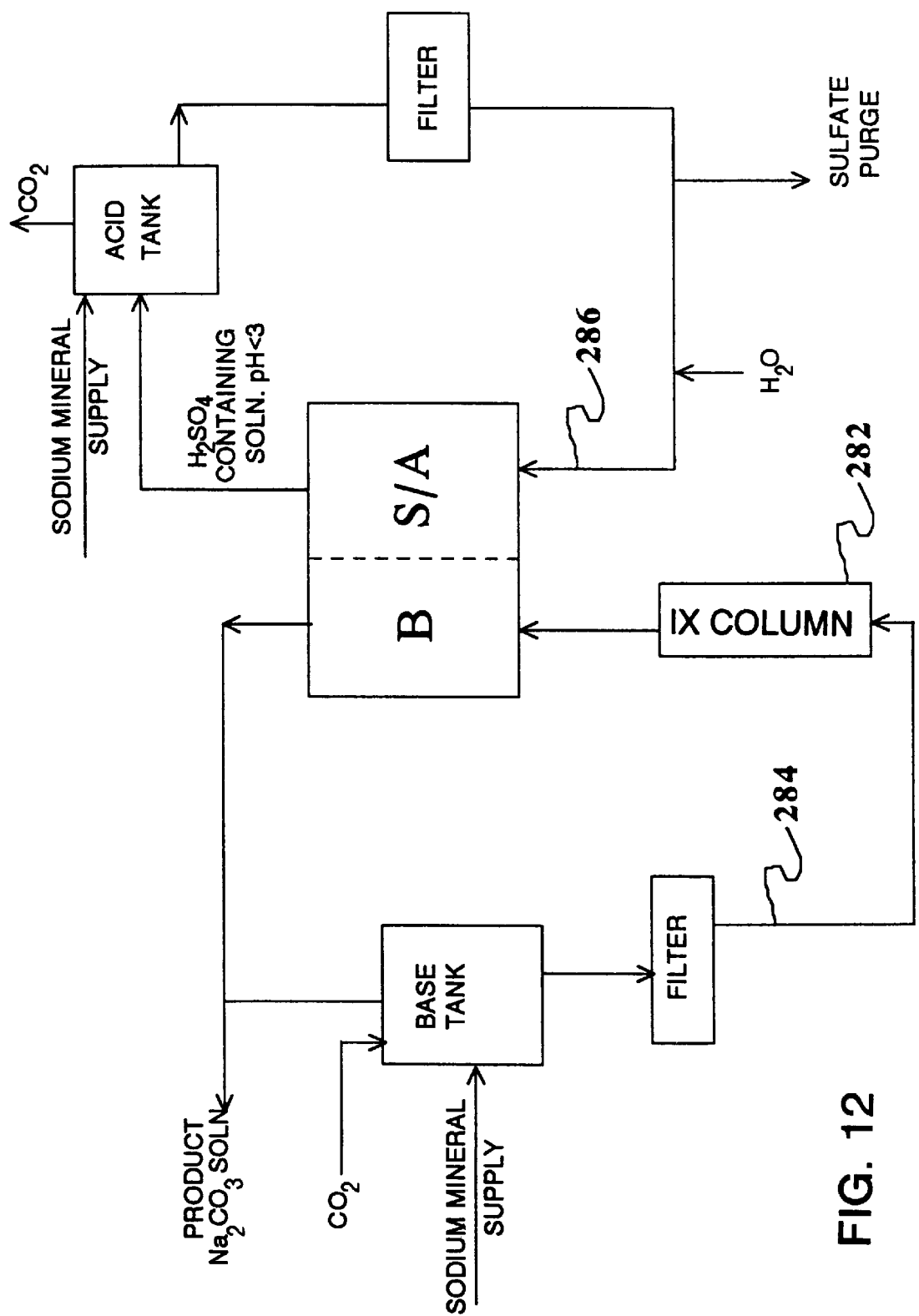
FIG. 12 is a block diagram which depicts the applicability of the invention to the recovery of sodium carbonate from carbonate/bicarbonate containing mineral sources.

FIG. 12 shows the application of the inventive apparatus for processing impure bicarbonate/carbonate/sulfate containing streams to produce sodium carbonate. Commercially available sodium alkali minerals often have impurities such as sodium sulfate, sodium chloride and a certain amount of calcium and magnesium salts. In the ED process the mineral is acidified in the acid loop 286, thereby liberating carbon dioxide, while sodium hydroxide is generated in the base loop 284. The base loop product may be acidified with a carbon dioxide containing source to generate sodium carbonate or a similar alkaline product.

Once again the use an ion exchange column 282 in communication with the base loop 284 of the ED cell removes the multivalent ions, thereby assuring long term reliable operation of the overall process. Potassium sulfate streams may similarly be processed to yield potassium carbonate.

Figure 13:
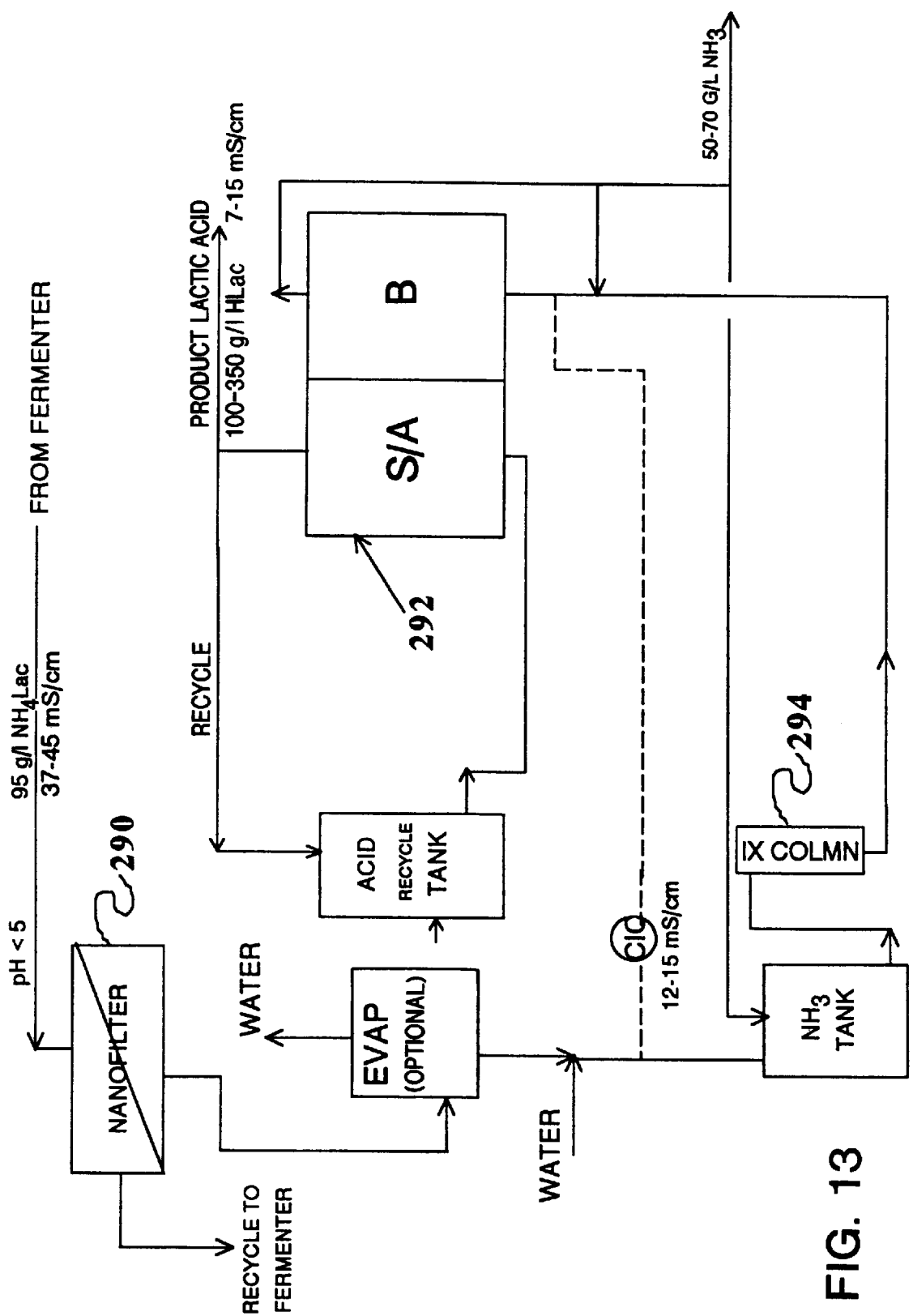
FIG. 13 is a block diagram which shows a system using the invention in conjunction with both a nanofiltered input feed and an ion exchange column at an output of said system.

FIG. 13 shows a process system that uses nanofiltration at 290 to remove a substantial part of the multivalent metals prior to a processing of the feed in the electrodialysis unit 292. The ion exchange column 294 is in the base loop in order to remove any residual metals that might enter the base loop, thereby enhancing the reliability of the overall process.

The combined apparatus of FIG. 13 is used with salts containing monovalent anions, e.g., sodium, potassium or ammonium chloride, lactate, acetate et. Also, the process using both nanofiltering and an ion exchange column is better suited for use in a two compartment cation (Shown in FIG. 13) cells or in three compartment cells. For two compartment anion cells, where the feed enters the salt/base loop, and the ion exchange column also located in the same loop, the benefit would appear to be less valuable.

Example 8

Briefly in review, the foregoing description shows that suitable apparatuses can attain and maintain a sufficiently low concentration of the divalent metals in the base loop. Hence, the precipitation of these divalent metals either does not occur or is not a serious problem, if it does occur. By maintaining low concentrations of the divalent metals in the base loop, their precipitation is averted, which has surprisingly beneficial effects such as the maintenance of a high and steady current throughput.

Also, the use of a cation membrane reduces the ratio of divalent metals relative to the amount of monovalent metals in the base loop, thereby reducing the cost of isolating the divalent metals. Moreover, the use of certain cation membranes allows transport of monovalent cations in preference to the multivalent cations, thus reducing the multivalent cation concentration in the base loop to a point where they do not precipitate in the base loop. The monovalent selective cation membranes (e.g. CMS from Tokuyama Soda) are most preferred for use in the apparatuses and processes of this invention.

FIG. 8 shows the solubility targets for calcium and magnesium for a base product of a given pH. A long term trouble free operation of the electrodialysis cell is obtained by maintaining the divalent metal concentrations in the base loop either below or near their solubility limits. The concentration targets are ~2–5 ppm for magnesium and 10–15 ppm for calcium in the high pH region of 12–14. Higher levels of Calcium and Magnesium can be present in the pH range of 9–11.

The pilot system described above was set up in the mode shown in FIG. 7, with the ion exchange column 206 in place. The electrodialysis cell contained eight AQ bipolar membranes and eight CMS cation (monovalent selective) membranes. The ion exchange column was regenerated with hydrochloric acid and placed in the ammonium form.

The ammonium lactate feed stream was ultrafiltered as in the earlier examples and was concentrated by evaporation to provide a ~250 gm/l lactate content prior to processing in the electrodialysis unit. The calcium content of the feed stream was higher than normal, possibly due to a dissolution of scale material from the evaporators.

Four batches were processed with the results summarized in the following Table 7. From tank 209, de-ionized water was added to the base loop at a rate of 8 ml/min. The slightly higher level of lactic diffusion to the base loop provided an adequate conductivity (>15 mS/cm) for producing a reliable cell stack operation. The base loop product contained 35–65 gm/l of ammonia and produced a pH ranging from 9.5 to 11.

TABLE 7

| Batch # | Duration hr. | Metals in acid, ppm | | Ammonia removal, % | Average values Current Voltage | | Current Efficiency % | Metals retention (overall) in acid, % | | Average metals content in base product, ppm | |
|---|---|---|---|---|---|---|---|---|---|---|---|
| | | Ca | Mg | | A | B | | Ca | Mg | Ca | Mg |
| 1 | 31.2 | 1310 | 143 | 93 | 45 | 23.6 | 56 | 92 | >99 | 1.5 | 0.3 |
| 2 | 34 | 1330 | 141 | 94 | 45 | 21.4 | 59 | 98 | >99 | 3.0 | 0.6 |
| 3 | 51.6 | 1250 | 179 | 94 | 45 | 22.5 | ~50 | 98 | >99 | 4.5 | 1.0 |
| 4 | 31.2 | 1100 | 180 | 94 | 50 | 24 | 61 | 99 | >99 | 5 | 1 |

The excellent retention shown by the monovalent selective cation membrane significantly reduced the load on the ion exchange column. The combination of this cation membrane and the ion exchange column was able to totally eliminate membrane and cell fouling problems; and this, in terms, results in surprisingly high current throughput, low cell voltage, as well as reproducible cell operation; despite the relatively high levels of calcium in the feed lactate.

Example 9

The pilot cell was set up in the mode shown in FIG. 7 with the ion exchange column removed from the base loop. The concentrated ammonium lactate feed stream used in the previous example was diluted with de-ionized water to reduce its lactic and multivalent metals concentration. Nine batches were processed as shown in the following Table 8. An aqueous solution was added to the base loop at a rate of 10 ml/min for the first 8 batches and 16 ml/min for the last batch 9 (due to the higher metals concentration in the last batch 9 feed side). The lactate in the feed stream ranged from 120 to 155 gm/l for the first 8 batches and was 244 gm/l for batch 9. The base loop product once again contained 35–65 gm/l of ammonia with a pH range from 9.5 to ~11. The base loop conductivity was maintained at 8–15 mS/cm at a minimum through addition of dilute ammonium sulfate or sulfuric acid if necessary.

branes were in excellent condition, showing no evidence of fouling. There were small amounts of calcium precipitates in the base loop. Evidently, this is because the base loop calcium concentration was 87–97.5 ppm in the above trials, which is above its solubility levels of 20–45 ppm in the pH range of operation (FIG. 8).

A use of larger amounts of dilution water to the base loop and/or a reduction in the amount of calcium in the feed stream salt would essentially eliminate the precipitation problems. Therefore, in the present example, assuming no further dilution of the base product, the feed containing 150 gm/l lactate should contain no more than ~125 ppm calcium and ~90 ppm magnesium. Those levels of the divalent metals are readily realized in actual fermentation operations. Hence, a process following this guideline would operate over very long operating periods without any fouling problems.

In this and other examples, the multivalent metals concentrations and their retention by the monovalent selective cation membrane have been stated in somewhat absolute terms. In reality, any given process solution contains a variety of cations, all of which will be transported across the cation membranes in proportion to the membrane's selectivity (or transport number) for the various cations.

Hence, a more accurate definition of the feed stream purity target is the ratio of the multivalent to monovalent

TABLE 8

| Batch # | Duration hr. | Metals in acid, ppm | | Ammonia removal, % | Average values Current Voltage | | Current Efficiency % | Metals retention (overall) in acid, % | | Average metals content in base product, ppm | |
|---|---|---|---|---|---|---|---|---|---|---|---|
| | | Ca | Mg | | A | B | | Ca | Mg | Ca | Mg |
| 1 | 31 | 506 | 92 | 90 | 45 | 26.5 | 52 | 97 | 98 | 92.3 | 3.81 |
| 2 | 35.8 | 506 | 94 | 90.5 | 45 | 26 | 54 | 93 | >99 | 90 | 3.8 |
| 3 | 31 | 510 | 94 | 90.5 | 45 | 26 | 51 | 93 | >99 | 93.5 | 3.9 |
| 4 | 24.8 | 500 | 94.6 | 91 | 45 | 25.5 | 53.4 | 97 | 99 | 97.5 | 4.2 |
| 5 | 36.2 | 503 | 94.4 | 90.8 | 45 | 26 | 62.2 | 95.5 | >99 | 88.6 | 3.8 |
| 6 | 27 | 420 | 75 | 87 | 45 | 27 | 52.3 | >95 | >99 | 94 | 3.8 |
| 7 | 27 | 410 | 64 | 89.5 | 45 | 26 | 51 | 96.5 | 97 | 92 | 3.2 |
| 8 | 26.9 | 397 | 62 | 89.3 | 45 | 26 | 48 | 96 | >99 | 92 | 3.2 |
| 9 | 35.5 | 771 | 146 | 92 | 45 | 25 | 67 | 98 | 99.5 | 87 | 3.7 |

The average metals content reported in the last column of Table 8 was calculated from the average retention for calcium and magnesium for the 9 batches and the total volumetric output from the base loop. It can be seen that in terms of current throughput, voltage and current, the efficiency of the cell performance was quite reproducible.

At the conclusion of the nine batches, the cell was opened and the internal structures were examined. All of the memmetals content in the feed stream. In the present example, the feed has 150 gm/l of lactic as lactate; i.e. 1.67 gram equivalents/liter. Therefore, at a near neutral pH of ~5, the feed has 1.67 gram equivalents/liter of ammonium ions. As a result the target divalent metals concentrations can be restated as ~75 ppm and ~55 ppm of magnesium per gram equivalent of ammonium ions in the feed solution.

In a similar fashion, the retention ability of the cation membrane is a function of the ratio of the monovalent to multivalent cations in the feed salt. As the feed salt gets depleted of monovalent cation content in the electrodialysis cell, the ratio of the monovalent to multivalent cations in the feed decreases. The term relative transport number (RTN) is often used to define the performance of the cation membrane:

$$RTN^M Ca = \frac{t^M / t^{Ca}}{C_M / C_{ca}}$$

wherein:
M: monovalent ion $NH_4^+$, Na, K or their total concentration
$t^M$: transport number of M ion in the cation membrane
$t^{Ca}$: transport number of Ca ion in the cation membrane
$C_m$: concentration of M ion in solution
$C_{ca}$: concentration of calcium ion in solution A suitable monovalent selective membrane for the process of this invention should exhibit an RTN relative to calcium of 6 or higher, preferably 8 or higher, and should yield the >90% retention, as shown in the above examples. CMS, a monovalent selective membrane made from polymeric materials satisfies this criterion. In reality the monovalent selective membranes may be made of organic or inorganic materials or combinations thereof. For example a ceramic membrane made of sodium super ion conductor (NaSICON) made by Ceramatec (Separation Science and Technology, 32 (1–4), pp 557–572, 1997) has the ability to transport of monovalent cations (sodium) and exclude the transport of multivalent cations or even large monovalent cations such as cesium; and would therefore have a large RTN. By way of comparison, a typical monovalent favoring membrane such as CMV has a RTN of ~1, while other cation membranes such as the AQ cation have even lower RTN values.

Figure 10A:
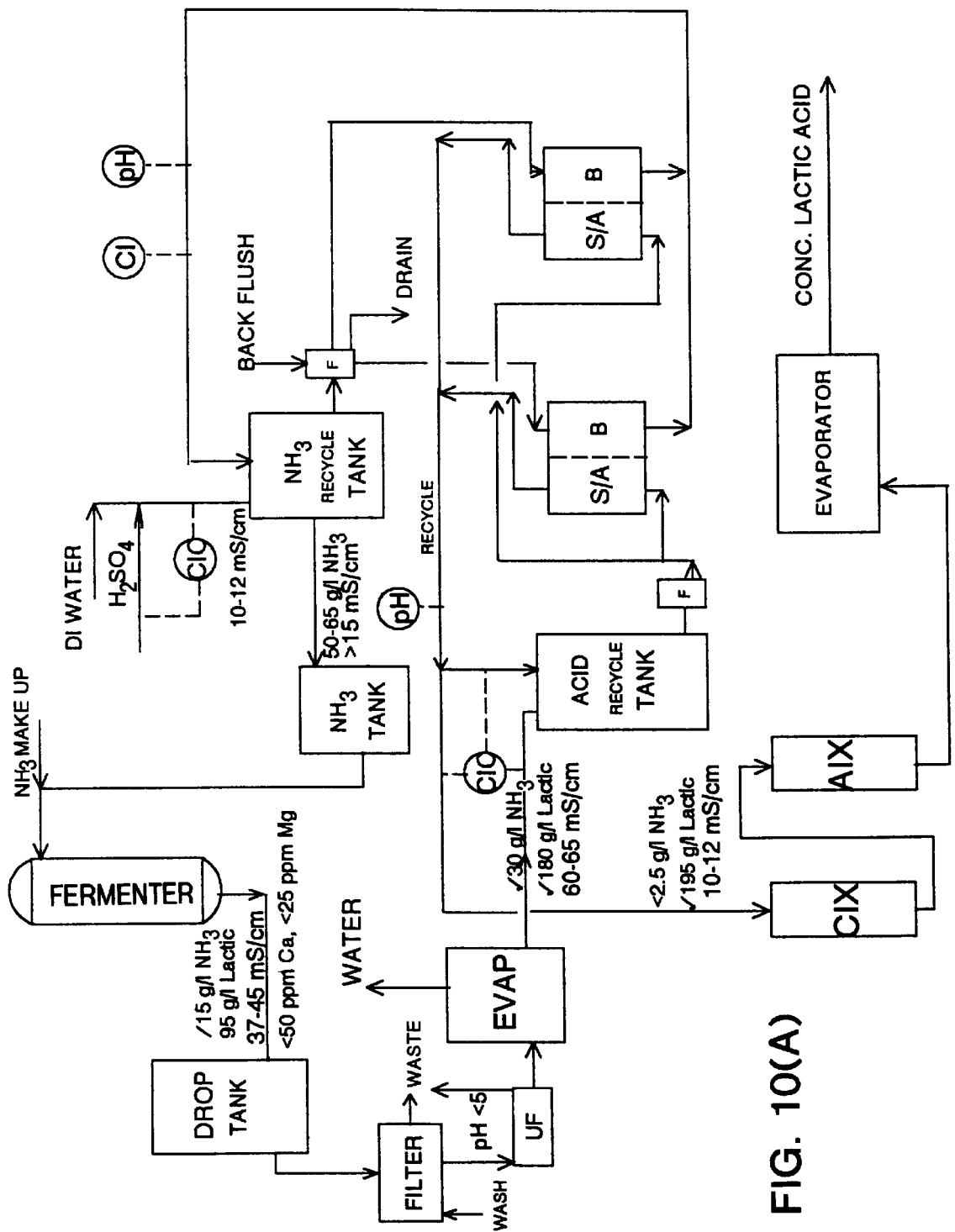

FIG. 10(a) shows the use of the two compartment cation cell using the monovalent selective cation membranes in the production of lactic acid from ammonium lactate. The lactate salt from the fermenter contains ~95 gm/l of lactic, as the lactate salt, and ~12–17 gm/l ammonia. The ammonium lactate is suitably filtered to remove the insoluble (cell mass) material. The lactate from the fermenter would typically contain <50 ppm calcium and 25–50 ppm magnesium in the form of soluble salts.

The filtered lactate solution is optionally concentrated via evaporation to >180 gm/l lactic content and processed in the two compartment electrodialysis cells. Dilution water optionally containing small amounts of sulfuric acid (typically ~0.1 wt % acid concentration) or some other suitable salt for providing conductivity is added to the base loop in order to pick up the ammonia that is produced. The ammonia solution from the base loop of the electrodialysis cells is collected in an $NH_3$ storage tank for possible reuse in the fermenter.

The acidified product from the electrodialysis cells typically contains <2.5 gm/l of ammonia equivalent and has pH of 2.7–2.9; representing 90% or a higher level of ammonia removal. This acidified product is further purified via a cation exchange (CIX) to remove the remaining ammonium and multivalent cations. The product from CIX is then treated in an anion exchange column (AIX) to remove substantially all the extraneous anions (e.g. sulfate, chloride, phosphate), and further concentrated as needed for sale.

Example 10

The utility of the process and apparatus using monovalent selective cation membranes is generic to all soluble salt feed stream solutions containing specific low levels of divalent metals contaminants. Such levels maybe obtained via a simple pH adjustment and a polishing filtration. For example, in the production of dilute sodium hydroxide and hydrochloric acid from salt (e.g. sodium chloride or sodium sulfite, other salts of monovalent cations), the feed stream salt solution can readily be purified via pH adjustment to about 10 with sodium hydroxide/carbonate and then filtered to yield a 10–25 wt % solution containing less than about 10 ppm calcium and ≦1 ppm magnesium. In prior art, this feed stream is further treated via a chelating resin ion exchange to further reduce the calcium content to 0.5 ppm or lower, prior to processing in the electrodialysis cell.

The improved process and apparatus disclosed in this application makes it feasible to eliminate the ion exchange pre-treatment step and to directly process this feed in a two compartment cation cell or a three compartment cell that uses monovalent selective cation membranes.

Figure 14:
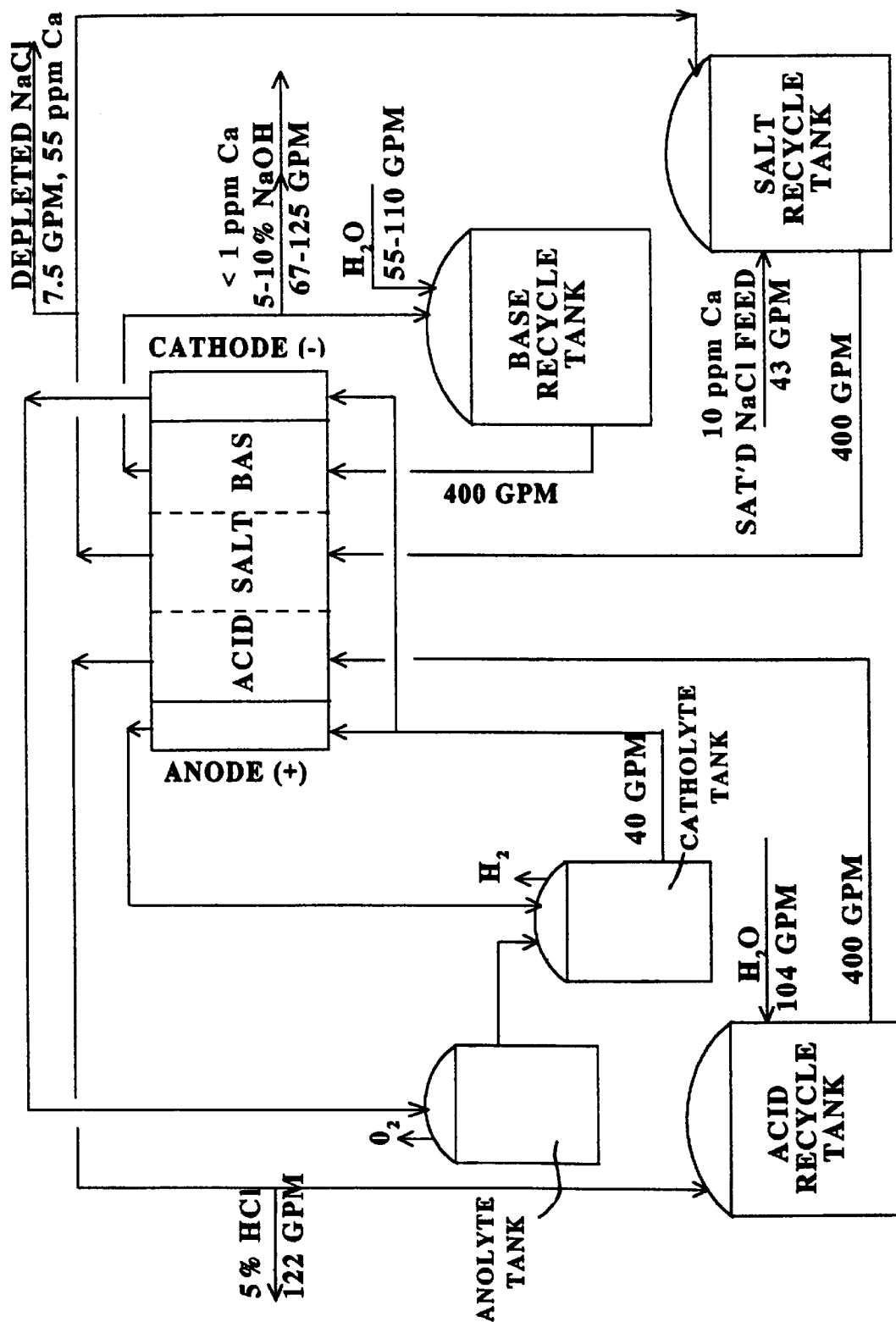
FIG. 14 is a flow chart showing a process for producing sodium hydroxide and hydrochloric acid.

FIG. 14 shows a flow sheet of a process for producing 40 tons/day of sodium hydroxide (typical) and 36.5 tons/day of hydrochloric acid. The feed stream salt containing 10 ppm calcium and 1 ppm magnesium is fed to the salt loop of a three compartment cell. The bulk of the salt feed is converted into the acid and base components in an electrodialysis cell that contains the monovalent selective cation membranes. These membranes retain the bulk (typically 95% or higher) of the divalent cations in the salt loop. These cations are purged from the salt loop as part of a depleted salt solution. In the example shown in FIG. 14, the depleted salt solution contains 96% of the divalent cations present in the original feed stream, which translates to about 55 ppm calcium in the depleted salt solution.

If desired, this depleted salt solution can be saturated with solid salt and purified via a pH adjustment and filtration to remove the excess multivalent metals. Then the purified solution is reused in the electrodialysis cell. Dilution water is used in the base loop to pick up the sodium hydroxide generated there.

This combination of monovalent selective membranes and the use of dilution water reduces the concentration of calcium in the base loop to <1 ppm (and a much lower concentration of magnesium), thereby ensuring an operation of the process and membranes in a non-fouling manner.

Example 11

Five batch tests were carried out by using ultrafiltered ammonium lactate feed solutions. The batch lasted a total of ~80 hours. The lactate feed stream was relatively low in divalent metals. The feed lactate was processed in a two compartment cell containing AQ bipolar membranes and CMT cation membranes. The cation membranes are of the "monovalent favoring" type (as opposed to CMS cation membranes which are a "monovalent selective" type).

A steady stream of make up liquid was maintained in the base loop helps retain the transported metals substantially in solution as well as facilitating their removal with the overflow. The make up liquid was 10 ml/min of dilute ammonium sulfate for the first four batches and DI water for the fifth batch. The results are summarized below:

TABLE 9

| Batch # | Duration hr. | Current, A Start | Current, A End | Voltage, V Start | Voltage, V End | Calcium in feed, ppm | Magnesium in feed, ppm | Lactic in acid, gm/l Start | Lactic in acid, gm/l End | Ammonia content in acid, gm/l Start | Ammonia content in acid, gm/l End |
|---|---|---|---|---|---|---|---|---|---|---|---|
| 1 | 16.8 | 40 | 31.4 | 22.8 | 38 | 20.9 | 52 | 109 | 117 | 17.2 | 1.67 |
| 2 | 18.5 | 40 | 23 | 23.2 | 38 | 29 | 47.9 | 105 | 95 | 14.9 | 1.14 |
| 3 | 5.4 | 40 | 40 | 23.9 | 38 | 70 | 23.2 | 110 | 100 | 12.7 | 0.67 |
| 4 | 17.8 | 40 | 33 | 23.0 | 38 | 71.2 | 22.6 | 9.4 | 101 | 12.6 | 0.87 |
| 5 | 22.5 | 40 | 26 | 23.5 | 30 | 67 | 24 | 82 | 85 | 10.7 | 0.2 |

It can be seen that the combination of a low concentration divalent metals in the feed stream and the use of diluent liquid in the base loop was able to give essentially reproducible cell performance, as evidenced by the similar voltages and currents at the start of each batch. The reproducibility is in fact quite good, considering that some of the batches went to high conversions, resulting in significant transport of the divalent metals out of the acid loop.

Those who are skilled in the art will readily perceive how to modiy the invention. Therefore, the appended claims are to be construed to cover all equivalent structures which fall within the true scope and spirit of the invention.

What is claimed is:

1. A process for converting an incoming feed of a salt of a monovalent cation and a weak acid anion into an acidified product stream which is reduced in its monovalent cation content, said process comprising the steps of:
   (a) obtaining an input feed stream which is freed of suspended solids;
   (b) passing the feed stream of step (a) through a salt/acid compartment of a two compartment electrodialysis cell containing at least a bipolar membrane and two cation membranes, said bipolar membrane having a cation side and an anion side, said salt/acid compartment being located between said cation side of the bipolar membrane and one of said cation membranes, the other of said two compartments being a base compartment coupled in a base loop extending directly from an output of said base compartment through an ion exchange column to an input of said base compartment, said base compartment being located between said anion side of the bipolar membrane and the other of said cation membranes;
   (c) supplying a liquid including water to the base compartment of the cell, said base compartment having an output stream in constant communication with said ion exchange column in said base loop, said column being packed with a material capable of removing multivalent cations that may enter the base loop whereby a first portion of an output stream from said base compartment passes through said ion exchange column for further refinement of said stream in said base compartment,
   (d) passing a direct current through the electrodialysis cell for causing an acidification of the feed salt and a concurrent transport of monovalent cations to the base loop;
   (e) producing a base product through a combination of the transported cation with a hydroxyl ion generated by the bipolar membrane in the base loop; and
   (f) withdrawing a second portion of said output stream from said base compartment which comprises the acidified feed and the base product.

2. The process of claim 1 wherein the acid is an organic acid.

3. The process of claim 1 wherein the produced base is selected from a group comprising ammonia, sodium hydroxide, potassium hydroxide, potassium carbonate, sodium carbonate, sodium sulfite, potassium sulfite, or mixtures thereof.

4. The process of claim 1 wherein the salt which is processed is an ammonium salt selected from a group consisting of an organic and an inorganic acid, said acid being at least partially water soluble.

5. The process of claim 1 where the acid which is produced is an organic or inorganic acid and the base which is produced is ammonia.

6. The process claim 1 wherein the cation membrane is selected from a group consisting of a monovalent favoring membrane and a monovalent selective membrane.

7. The process of claim 1 wherein the cation membrane is selected from a group consisting of a monovalent favoring and a monovalent selective membrane and the step of maintaining the pH in the range of about 5 to about 14.

8. The process of claim 1 where the acid is a water soluble acid selected from a group consisting of monoorganic, diorganic, and trivalent organic acid.

9. The process of claim 1 wherein an acidifying agent is added into the base loop to maintain the pH in the range of 7–13.5.

10. The process of claim 1 wherein an acidifying agent is added to the base loop to maintain the pH in the range of about 8–11 within the base loop.

11. The process of claim 1 wherein the feed stream is selected from a group consisting of an ammonium, sodium, potassium salt or mixtures thereof.

12. The process of claim 1 wherein the pH of the feed stream salt solution is adjusted to a value greater than about 9 and is filtered to remove precipitated multivalent compounds prior to processing in the electrodialysis cell.

13. The process of claim 1 wherein the pH of the feed stream salt solution is adjusted to a value greater than about 9 and filtered to remove precipitated multivalent compounds prior to processing in the electrodialysis cell.

14. The process of claim 13 wherein the salt is selected from a group consisting of sodium chloride, potassium chloride, sodium sulfate, potassium sulfate, sodium nitrate, potassium nitrate, sodium phosphate, potassium phosphate, or mixtures thereof.

15. The process of claim 1 wherein the weak acid anion is organic, and taken from a class consisting of lactate, formate, acetate and the cation is sodium, potassium, ammonium.

16. The process of claim 1 wherein the weak acid anion is bisulfite, sulfite mixtures thereof.

17. The process of claim 1 wherein the weak acid anion is carbonate, bicarbonate or mixtures thereof.

18. A process for converting an incoming feed of a weak base monovalent cation and an anion into a basified product stream which is reduced in its anion content, said process comprising the steps of:

(a) obtaining an input feed stream which is freed of suspended solids;

(b) passing the feed stream of step (a) through a salt/base compartment of a two compartment electrodialysis cell containing at least a bipolar membrane and an anion membrane, said bipolar membrane having a cation side and an anion side, said salt/base compartment being coupled in a salt/base loop extending directly from an output of said salt/base compartment through an ion exchange column to an input of said salt/base compartment, located between said anion side of the bipolar membrane and said anion membrane, the other of said two compartments being an acid compartment, said acid compartment being located between said cation side of the bipolar membrane and an anion membrane;

(c) supplying a liquid including water to the base compartment of the cell and the feed stream from step (a) to the salt/base loop, said salt/base loop having an output stream in constant communication with said ion exchange column in said salt/base loop, said column being packed with a material capable of removing multivalent cations that may enter the base loop whereby a first portion of an output stream from said salt/base loop passes through said ion exchange column for further refinement of said stream in said salt/base compartment;

(d) passing a direct current through the electrodialysis cell for causing a basification of the feed salt and a concurrent transport of anions to the acid loop; and (e) withdrawing a second portion of said output stream from said salt/base compartment which comprises the basified salt and an acid product from the acid compartment.

19. The process of claim 18 wherein the weak base anion is ammonium and the anion is lactate, formate, acetate; said salt solution being obtained via fermentation of a suitable substrate such as glucose.

20. A process for converting an incoming feed of a salt of a monovalent cation and an anion into acid and base product streams and a stream reduced in its monovalent salt content, said process comprising the steps of:

(a) obtaining an input feed stream which is freed of suspended solids;

(b) passing the feed stream of step (a) through a salt compartment of a three compartment electrodialysis cell containing at least a bipolar membrane, a cation membrane and an anion membrane, said bipolar membrane having a cation side and an anion side, said salt compartment being located between said cation membrane and the anion membrane, and said acid compartment being located between said cation side of the bipolar membrane and said anion membrane; and the base compartment being located between the anion side of the bipolar membrane and the cation membrane; said base compartment being coupled in a base loop extending directly from an output of said base compartment through an ion exchange column to an input of said base compartment;

(c) supplying a liquid including water to the acid and base compartments of the cell, said base compartment having an output stream in constant communication with said ion exchange column in said base loop, said column being packed with a material capable of removing multivalent cations that may enter the base loop whereby a first portion of an output stream from said base compartment passes through said ion exchange column for further refinement of said stream in said base compartment;

(d) passing a direct current through the electrodialysis cell for causing conversion of at least a portion of the feed salt into its acid and base components through transport of monovalent cations to the base loop and anions to an acid loop;

(e) producing an acid product through a combination of the transported anion with a hydrogen ion generated by this bipolar membrane in the acid loop and a base product through a combination of the transported cation with a hydroxyl ion generated by the bipolar membrane in the base loop; and (f) withdrawing the feed depleted in its salt content; the acid product and a second portion of said output stream from said base compartment which comprises the acidified feed and the base product.

21. The process of claim 20 wherein the feed is sodium chloride, sodium sulfate.

* * * * *